United States Patent
Garfield et al.

(10) Patent No.: US 10,894,317 B2
(45) Date of Patent: Jan. 19, 2021

(54) AUTOMATED COMPOUNDING EQUIPMENT FOR CLOSED FLUID TRANSFER SYSTEM

(71) Applicant: J&J Solutions, Inc., Coralville, IA (US)

(72) Inventors: Jared Garfield, North Liberty, IA (US); Dana Schramm, Woodbury, MN (US); Gregory Lyon, Mamaroneck, NY (US); Scott Schuler, Sr., Coralville, IA (US)

(73) Assignee: CORVIDA MEDICAL, INC., Coralville, IA (US)

( * ) Notice: Subject to any disclaimer, the term of this patent is extended or adjusted under 35 U.S.C. 154(b) by 246 days.

(21) Appl. No.: 15/767,438

(22) PCT Filed: Oct. 13, 2016

(86) PCT No.: PCT/US2016/056776
§ 371 (c)(1),
(2) Date: Apr. 11, 2018

(87) PCT Pub. No.: WO2017/066406
PCT Pub. Date: Apr. 20, 2017

(65) Prior Publication Data
US 2018/0297193 A1    Oct. 18, 2018

Related U.S. Application Data

(60) Provisional application No. 62/240,650, filed on Oct. 13, 2015.

(51) Int. Cl.
*B25J 9/02*        (2006.01)
*A61M 1/00*        (2006.01)
(Continued)

(52) U.S. Cl.
CPC ............... *B25J 9/026* (2013.01); *A61J 3/002* (2013.01); *A61M 1/00* (2013.01); *B25J 9/04* (2013.01);
(Continued)

(58) Field of Classification Search
CPC ...... B25J 15/10; B25J 15/026; B25J 15/0042; B25J 9/04; B25J 9/026; A61M 1/00; A61J 3/002
See application file for complete search history.

(56) References Cited

U.S. PATENT DOCUMENTS 2,530,230 A    11/1950  Cozzoli
3,270,996 A     9/1966  Churchill et al.
(Continued)

FOREIGN PATENT DOCUMENTS

CN    202825572 U    3/2013
CN    103007371 A    4/2013
(Continued)

OTHER PUBLICATIONS

Chou, C.K. (1995); "Radiofrequency Hyperthermia in Cancer Therapy"; Biologic Effects of Nonionizing Electromagnetic Fields; Chapter 94; CRCPress, Inc.; pp. 1424-1428.
(Continued)

*Primary Examiner* — Timothy L Maust
(74) *Attorney, Agent, or Firm* — Carter, DeLuca & Farrell LLP; Francesco Sardone, Esq.

(57) ABSTRACT

An automatic or semi-automatic preparation system process is provided for forming a medicament solution from a vial containing one of a liquid and a non-liquid material.

9 Claims, 28 Drawing Sheets

(51) Int. Cl.
*B25J 15/10* (2006.01)
*G05B 19/18* (2006.01)
*A61J 3/00* (2006.01)
*B25J 15/00* (2006.01)
*B25J 9/04* (2006.01)
*B25J 15/02* (2006.01)

(52) U.S. Cl.
CPC ......... *B25J 15/0042* (2013.01); *B25J 15/026* (2013.01); *B25J 15/10* (2013.01); *G05B 19/18* (2013.01)

(56) References Cited

U.S. PATENT DOCUMENTS

| | | |
|---|---|---|
| 3,706,305 A | 12/1972 | Berger et al. |
| 4,180,070 A | 12/1979 | Genese |
| 4,201,208 A | 5/1980 | Cambio, Jr. |
| 4,576,211 A | 3/1986 | Valentini et al. |
| 4,579,380 A | 4/1986 | Zaremsky et al. |
| 4,673,404 A | 6/1987 | Gustavsson |
| 4,692,068 A | 9/1987 | Hanrot et al. |
| 4,752,292 A | 6/1988 | Lopez et al. |
| 5,100,394 A | 3/1992 | Dudar et al. |
| 5,135,489 A | 8/1992 | Jepson et al. |
| 5,158,554 A | 10/1992 | Jepson et al. |
| 5,167,648 A | 12/1992 | Jepson et al. |
| 5,188,620 A | 2/1993 | Jepson et al. |
| 5,211,638 A | 5/1993 | Dudar et al. |
| 5,312,377 A | 5/1994 | Dalton |
| 5,314,466 A | 5/1994 | Stern et al. |
| 5,344,441 A | 9/1994 | Gronauer |
| 5,370,678 A | 12/1994 | Edwards et al. |
| 5,405,340 A | 4/1995 | Fageol et al. |
| 5,409,453 A | 4/1995 | Lundquist et al. |
| 5,431,201 A * | 7/1995 | Torchia ............ A61J 1/20 141/100 |
| 5,437,650 A | 8/1995 | Larkin et al. |
| 5,445,630 A | 8/1995 | Richmond |
| 5,470,327 A | 11/1995 | Helgren et al. |
| 5,507,733 A | 4/1996 | Larkin et al. |
| 5,520,666 A | 5/1996 | Choudhury et al. |
| 5,545,152 A | 8/1996 | Funderburk et al. |
| 5,549,566 A | 8/1996 | Elias |
| 5,580,351 A | 12/1996 | Helgren et al. |
| 5,658,260 A | 8/1997 | Desecki et al. |
| 5,685,842 A | 11/1997 | Drivas |
| 5,685,866 A | 11/1997 | Lopez |
| 5,702,374 A | 12/1997 | Johnson |
| 5,776,176 A | 7/1998 | Rudie |
| 5,785,682 A | 7/1998 | Grabenkort |
| 5,785,692 A | 7/1998 | Attermeier et al. |
| 5,797,897 A | 8/1998 | Jepson et al. |
| 5,800,486 A | 9/1998 | Thome et al. |
| 5,807,345 A | 9/1998 | Grabenkort |
| 5,810,768 A | 9/1998 | Lopez |
| 5,861,021 A | 1/1999 | Thome et al. |
| 5,871,500 A | 2/1999 | Jepson et al. |
| 5,891,129 A | 4/1999 | Daubert et al. |
| 5,899,888 A | 5/1999 | Jepson et al. |
| 5,924,584 A | 7/1999 | Hellstrom et al. |
| 5,954,104 A | 9/1999 | Daubert et al. |
| 5,954,708 A | 9/1999 | Lopez et al. |
| 5,957,898 A | 9/1999 | Jepson et al. |
| 5,964,785 A | 10/1999 | Desecki et al. |
| 6,063,068 A | 5/2000 | Fowles et al. |
| 6,083,194 A | 7/2000 | Lopez |
| 6,090,091 A | 7/2000 | Fowles et al. |
| 6,113,068 A | 9/2000 | Ryan |
| 6,135,168 A * | 10/2000 | Yang ............ H01L 21/67373 141/91 |
| 6,139,534 A | 10/2000 | Niedospial, Jr. et al. |
| 6,161,049 A | 12/2000 | Rudie et al. |
| 6,171,287 B1 | 1/2001 | Lynn et al. |
| 6,193,697 B1 | 2/2001 | Jepson et al. |
| 6,213,996 B1 | 4/2001 | Jepson et al. |
| 6,221,065 B1 | 4/2001 | Davis |
| 6,245,048 B1 | 6/2001 | Fangrow, Jr. et al. |
| 6,261,266 B1 | 7/2001 | Jepson et al. |
| 6,261,282 B1 | 7/2001 | Jepson et al. |
| 6,302,289 B1 | 10/2001 | Andersson et al. |
| 6,344,033 B1 | 2/2002 | Jepson et al. |
| 6,382,442 B1 | 5/2002 | Thibault et al. |
| 6,387,074 B1 | 5/2002 | Horppu et al. |
| 6,394,983 B1 | 5/2002 | Mayoral et al. |
| 6,409,708 B1 | 6/2002 | Wessman |
| 6,428,520 B1 | 8/2002 | Lopez et al. |
| 6,447,498 B1 | 9/2002 | Jepson et al. |
| 6,506,189 B1 | 1/2003 | Rittman, III et al. |
| 6,522,930 B1 | 2/2003 | Schaer et al. |
| 6,524,295 B2 | 2/2003 | Daubert et al. |
| 6,569,125 B2 | 5/2003 | Jepson et al. |
| 6,577,903 B1 | 6/2003 | Cronin et al. |
| 6,595,964 B2 | 7/2003 | Finley et al. |
| 6,599,273 B1 | 7/2003 | Lopez |
| 6,605,076 B1 | 8/2003 | Jepson et al. |
| 6,605,576 B2 | 8/2003 | Lee |
| 6,635,043 B2 | 10/2003 | Daubert et al. |
| 6,635,044 B2 | 10/2003 | Lopez |
| 6,635,055 B1 | 10/2003 | Cronin |
| 6,647,935 B2 | 11/2003 | Aoyama et al. |
| 6,660,527 B2 | 12/2003 | Stroup |
| 6,669,681 B2 | 12/2003 | Jepson et al. |
| 6,684,918 B1 | 2/2004 | Thilly et al. |
| 6,695,817 B1 | 2/2004 | Fangrow, Jr. |
| 6,706,040 B2 | 3/2004 | Mahon et al. |
| D488,867 S | 4/2004 | Chau |
| 6,715,520 B2 | 4/2004 | Andreasson et al. |
| 6,752,154 B2 | 6/2004 | Fogarty et al. |
| 6,871,838 B2 | 3/2005 | Raines et al. |
| 6,874,522 B2 | 4/2005 | Anderson et al. |
| 6,875,205 B2 | 4/2005 | Leinsing |
| 6,887,235 B2 | 5/2005 | O'Connor et al. |
| 6,915,823 B2 | 7/2005 | Osborne et al. |
| 6,939,350 B2 | 9/2005 | Phan |
| 7,025,389 B2 | 4/2006 | Cuschieri et al. |
| 7,040,598 B2 | 5/2006 | Raybuck |
| 7,044,441 B2 | 5/2006 | Doyle |
| 7,100,891 B2 | 9/2006 | Doyle |
| 7,114,701 B2 | 10/2006 | Peppel |
| 7,118,590 B1 | 10/2006 | Cronin |
| 7,128,739 B2 | 10/2006 | Prakash et al. |
| 7,175,615 B2 | 2/2007 | Hanly et al. |
| 7,197,363 B2 | 3/2007 | Prakash et al. |
| 7,223,259 B2 | 5/2007 | Marshall et al. |
| 7,228,879 B2 * | 6/2007 | Miller ............ B05B 15/50 141/271 |
| 7,244,249 B2 | 7/2007 | Leinsing et al. |
| 7,306,198 B2 | 12/2007 | Doyle |
| 7,306,584 B2 | 12/2007 | Wessman et al. |
| 7,311,703 B2 | 12/2007 | Turovskiy et al. |
| 7,314,061 B2 | 1/2008 | Peppel |
| 7,316,669 B2 | 1/2008 | Ranalletta |
| 7,358,505 B2 | 4/2008 | Woodworth et al. |
| 7,396,051 B2 | 7/2008 | Baldwin et al. |
| 7,425,209 B2 | 9/2008 | Fowles et al. |
| 7,470,258 B2 | 12/2008 | Barker et al. |
| 7,497,848 B2 | 3/2009 | Leinsing et al. |
| 7,497,849 B2 | 3/2009 | Fangrow, Jr. |
| 7,503,908 B2 | 3/2009 | Bartholomew |
| 7,510,545 B2 | 3/2009 | Peppel |
| 7,563,253 B2 | 7/2009 | Tanner et al. |
| 7,569,036 B2 | 8/2009 | Domkowski et al. |
| 7,569,043 B2 | 8/2009 | Fangrow |
| 7,591,449 B2 | 9/2009 | Raines et al. |
| 7,615,035 B2 | 11/2009 | Peppel |
| 7,645,271 B2 | 1/2010 | Fangrow |
| 7,645,274 B2 | 1/2010 | Whitley |
| 7,651,481 B2 | 1/2010 | Raybuck |
| 7,670,326 B2 | 3/2010 | Shemesh |
| 7,713,247 B2 | 5/2010 | Lopez |
| 7,717,883 B2 | 5/2010 | Lopez |
| 7,717,884 B2 | 5/2010 | Lopez |
| 7,717,886 B2 | 5/2010 | Lopez |

(56) References Cited

U.S. PATENT DOCUMENTS

| | | | |
|---|---|---|---|
| 7,743,799 B2 | 6/2010 | Mosler et al. | |
| 7,744,581 B2 | 6/2010 | Wallen et al. | |
| 7,753,085 B2* | 7/2010 | Tribble | B65B 3/003 |
| | | | 141/2 |
| 7,753,338 B2 | 7/2010 | Desecki | |
| 7,758,560 B2 | 7/2010 | Connell et al. | |
| 7,762,524 B2 | 7/2010 | Cawthon et al. | |
| 7,763,013 B2 | 7/2010 | Baldwin et al. | |
| 7,763,199 B2 | 7/2010 | Fangrow, Jr. | |
| 7,766,304 B2 | 8/2010 | Phillips | |
| 7,766,897 B2 | 8/2010 | Ramsey et al. | |
| 7,824,393 B2 | 11/2010 | Fangrow | |
| 7,900,659 B2 | 3/2011 | Whitley et al. | |
| 8,043,864 B2 | 10/2011 | Stroup | |
| 8,119,419 B2 | 2/2012 | Stroup | |
| 8,122,923 B2 | 2/2012 | Kraus et al. | |
| 8,251,346 B2 | 8/2012 | Stroup | |
| 8,287,513 B2 | 10/2012 | Ellstrom et al. | |
| 8,414,554 B2 | 4/2013 | Garfield et al. | |
| 8,414,555 B2 | 4/2013 | Garfield et al. | |
| 8,414,556 B2 | 4/2013 | Garfield et al. | |
| 8,469,940 B2 | 6/2013 | Garfield et al. | |
| 8,545,475 B2 | 10/2013 | Wallen | |
| 8,894,627 B2 | 11/2014 | Garfield et al. | |
| 8,913,645 B2 | 12/2014 | Sabourdy et al. | |
| 9,039,047 B2 | 5/2015 | Imai | |
| 9,082,979 B2 | 7/2015 | Malek et al. | |
| 9,107,809 B2 | 8/2015 | Garfield et al. | |
| 9,186,494 B2 | 11/2015 | Fangrow | |
| 9,220,661 B2 | 12/2015 | Garfield et al. | |
| 9,351,906 B2 | 5/2016 | Garfield et al. | |
| 9,358,182 B2 | 6/2016 | Garfield et al. | |
| 9,364,396 B2 | 6/2016 | Garfield et al. | |
| 9,370,466 B2 | 6/2016 | Garfield et al. | |
| 9,381,137 B2 | 7/2016 | Garfield et al. | |
| 9,877,895 B2* | 1/2018 | Garfield | A61J 1/2003 |
| 2002/0115981 A1 | 8/2002 | Wessman | |
| 2002/0177819 A1 | 11/2002 | Barker et al. | |
| 2003/0070726 A1 | 4/2003 | Andreasson et al. | |
| 2003/0187420 A1 | 10/2003 | Akerlund et al. | |
| 2003/0191445 A1 | 10/2003 | Wallen et al. | |
| 2004/0124389 A1 | 7/2004 | Phillips | |
| 2004/0144668 A1 | 7/2004 | Marshall et al. | |
| 2004/0215147 A1 | 10/2004 | Wessman et al. | |
| 2006/0097371 A1 | 5/2006 | Kawasaki et al. | |
| 2006/0106360 A1 | 5/2006 | Wong | |
| 2006/0129109 A1 | 6/2006 | Shaw et al. | |
| 2007/0015233 A1 | 1/2007 | Brancia | |
| 2007/0079894 A1 | 4/2007 | Kraus et al. | |
| 2007/0088315 A1 | 4/2007 | Haindl | |
| 2007/0101772 A1 | 5/2007 | Duncan et al. | |
| 2007/0177819 A1 | 8/2007 | Ma et al. | |
| 2008/0097371 A1 | 4/2008 | Shemesh | |
| 2008/0103455 A1 | 5/2008 | Domkowski et al. | |
| 2008/0103485 A1 | 5/2008 | Kruger | |
| 2008/0114328 A1* | 5/2008 | Doherty | A61J 1/2096 |
| | | | 604/414 |
| 2008/0132854 A1 | 6/2008 | Sharp | |
| 2008/0142388 A1 | 6/2008 | Whitley et al. | |
| 2008/0172024 A1 | 7/2008 | Yow | |
| 2008/0223484 A1 | 9/2008 | Horppu | |
| 2008/0249479 A1 | 10/2008 | Zinger et al. | |
| 2008/0249498 A1 | 10/2008 | Fangrow | |
| 2008/0262465 A1 | 10/2008 | Zinger et al. | |
| 2008/0264450 A1 | 10/2008 | Baldwin et al. | |
| 2008/0287920 A1 | 11/2008 | Fangrow et al. | |
| 2008/0318456 A1 | 12/2008 | Yow et al. | |
| 2009/0069783 A1 | 3/2009 | Ellstrom et al. | |
| 2009/0216212 A1 | 8/2009 | Fangrow, Jr. | |
| 2009/0243281 A1 | 10/2009 | Seifert et al. | |
| 2009/0270832 A1 | 10/2009 | Vancaillie et al. | |
| 2009/0326506 A1 | 12/2009 | Hasegawa et al. | |
| 2010/0004602 A1 | 1/2010 | Nord et al. | |
| 2010/0004618 A1 | 1/2010 | Rondeau et al. | |
| 2010/0004619 A1 | 1/2010 | Rondeau et al. | |
| 2010/0004634 A1 | 1/2010 | Whitley | |
| 2010/0036330 A1 | 2/2010 | Plishka et al. | |
| 2010/0049160 A1 | 2/2010 | Jepson et al. | |
| 2010/0055668 A1 | 3/2010 | Stroup | |
| 2010/0106129 A1 | 4/2010 | Goeckner et al. | |
| 2010/0108681 A1 | 5/2010 | Jepson et al. | |
| 2010/0147402 A1 | 6/2010 | Tornqvist | |
| 2010/0152669 A1 | 6/2010 | Rosenquist | |
| 2010/0160889 A1 | 6/2010 | Smith et al. | |
| 2010/0217226 A1 | 8/2010 | Shemesh | |
| 2010/0218846 A1 | 9/2010 | Kriheli | |
| 2010/0241088 A1 | 9/2010 | Ranalletta et al. | |
| 2010/0249745 A1 | 9/2010 | Ellstrom | |
| 2011/0004185 A1 | 1/2011 | Hasegawa et al. | |
| 2011/0015580 A1 | 1/2011 | Stroup | |
| 2011/0049866 A1 | 3/2011 | Trombley, III et al. | |
| 2011/0112501 A1 | 5/2011 | Garfield et al. | |
| 2011/0266477 A1 | 11/2011 | Stroup | |
| 2012/0048676 A1 | 3/2012 | Giribona et al. | |
| 2012/0157914 A1 | 6/2012 | Stroup | |
| 2012/0325365 A1 | 12/2012 | Strangis | |
| 2013/0000780 A1 | 1/2013 | Garfield et al. | |
| 2013/0066293 A1 | 3/2013 | Garfield et al. | |
| 2014/0155894 A1 | 6/2014 | Dorawa et al. | |
| 2015/0068640 A1 | 3/2015 | Garfield et al. | |
| 2015/0209235 A1 | 7/2015 | Garfield et al. | |
| 2016/0243007 A1 | 8/2016 | Constantine et al. | |
| 2016/0250102 A1 | 9/2016 | Garfield et al. | |
| 2018/0008784 A1 | 1/2018 | Olson et al. | |
| 2018/0147118 A1 | 5/2018 | Garfield et al. | |

FOREIGN PATENT DOCUMENTS

| | | |
|---|---|---|
| CN | 104029025 A | 9/2014 |
| EP | 0050466 A1 | 4/1982 |
| EP | 0452220 A1 | 10/1991 |
| FR | 2944302 A1 | 10/2010 |
| FR | 2959878 A1 | 11/2011 |
| FR | 2959879 A1 | 11/2011 |
| JP | 08182742 | 7/1996 |
| JP | 2002126094 A | 5/2002 |
| WO | 9929415 A1 | 6/1999 |
| WO | 03088806 A2 | 10/2003 |
| WO | 2005002492 A1 | 1/2005 |
| WO | 2007101772 A1 | 9/2007 |
| WO | 2007120641 A2 | 10/2007 |
| WO | 2008136720 A1 | 11/2008 |
| WO | 2009035384 A1 | 3/2009 |
| WO | 2011124780 A2 | 10/2011 |
| WO | 2014007694 A1 | 1/2014 |
| WO | 2017049107 A1 | 3/2017 |
| WO | 2017066406 A1 | 4/2017 |

OTHER PUBLICATIONS

Urologix, Inc.—Medical Professionals: "Targis Technology"; http://www.urologix.com/medical/technology.html; Apr. 27, 2001; pp. 3.
International Search Report & Written Opinion of Int'l Appln. PCT/US2016/056776 dated Feb. 7, 2017.

* cited by examiner

AUTOMATED COMPOUNDING EQUIPMENT FOR CLOSED FLUID TRANSFER SYSTEM

CROSS-REFERENCE TO RELATED APPLICATIONS

The present application is a 35 U.S.C. § 371 National Phase Filing claiming the benefit of and priority to International Application No. PCT/US2016/056776, filed on Oct. 13, 2016, which claims the benefit of and priority to U.S. Provisional Application Ser. No. 62/240,650, filed on Oct. 13, 2015, the entire content of each is incorporated herein by reference.

BACKGROUND

1. Technical Field

The present disclosure relates generally to closed fluid transfer systems and their related components, and more particularly, to equipment, components and systems for the transfer of gases/liquids/fluid or other substances from a first container to a second container while maintaining a closed system.

2. Background of Related Art

In one instance, hazardous medicines are frequently applied in the treatment of certain diseases, in particular, for example, in the treatment of cancer. Cytotoxic drugs have generally been used to kill cancer cells. However, the use of cytotoxic drugs, in the treatment of cancer cells, presents specific dangers to all cells, both in the patient and in healthcare providers. Although the exposure to a health care provider is normally very small for each cytotoxic drug dose administration, evidence suggests that chronic, low-dose exposure can produce significant health problems. Accordingly, a system that allows the safe handling of hazardous drugs while significantly reducing and/or eliminating the exposure to providers would be of great benefit.

Drugs are typically supplied in glass or plastic vials that are capped with a gas impermeable liquid seal or stopper. In some instances, the vial contents are a solid powder, such that a liquid needs to be injected for mixing (e.g., reconstitution). The injection of additional contents (e.g., liquid) into the vial produces an increased pressure which stresses the seal or stopper. Although the vial is intended to be sealed to liquid and gases, drug molecules in vapor phase can leak or pass around the sides of the stopper or through the stopper as the injection needle is withdrawn, thus presenting a hazard to the provider or clinician.

Accordingly, with the potential for aerosol leakage, leakage/spraying upon needle withdrawal, or spills, a means with which to prevent the accidental vapor phase drug egress is required.

Thus, the need exists for new equipment, components and systems capable of transferring gases/fluids/liquids or other substances between a conventional syringe and one of a vial, a patient I.V. (intra-venous) set, or an I.V. bag without leaking or spilling and without exposure of the liquids to substances outside the closed system. As such, healthcare personnel may more safely use and handle fluid substances including potentially hazardous liquids and the like.

SUMMARY

The present disclosure relates to equipment, components and systems for the transfer of a fluid/substance from a first container to a second container while maintaining a closed system.

According to an aspect of the present disclosure, an automatic or semi-automatic preparation system for forming a medicament solution from a vial containing one of a liquid and a non-liquid material, is provided. The preparation system includes a frame configured to provide three axes of motion. The frame includes a plurality of vertical studs, each stud extending along a respective first axis; a plurality of first stringers extending between and interconnecting selected vertical studs, each first stringer extending along a respective second axis, wherein each second axis is orthogonal to the first axis; and a plurality of second stringers extending between and interconnecting selected vertical studs and selected first stringers, each second stringer extending along a respective third axis, wherein each third axis is orthogonal to the first axis and orthogonal to the second axis.

The preparation system further includes a gantry assembly translatably supported on at least one of the plurality of first stringers; a gantry translation assembly operatively connected to the gantry assembly, wherein actuation of the gantry translation assembly causes gantry assembly to translate along the at least one of the plurality of first stringers, in a direction parallel to the second axis; and a turntable assembly. The turntable assembly includes a platform translatably supported on gantry assembly; a turntable gear supported on the platform, wherein an axis of rotation of the turntable gear extends in a direction parallel to the first axis; a rail column depending from and non-rotatably connected to the turntable gear, the rail column extending in a direction parallel to the first axis; and a carriage translatably supported on the rail column.

The gantry translation assembly may include a threaded gantry rod rotatably supported on the frame, the threaded gantry rod being in threaded engagement with a nut structure of the gantry assembly; and a gantry translation motor connected to the threaded gantry rod for rotating the threaded gantry rod in a first direction and a second direction. In operation, rotation of the gantry translation motor in the first direction may cause the gantry assembly to translate in a first direction; and rotation of the gantry translation motor in the second direction may cause the gantry assembly to translate in a second direction.

The gantry assembly may include a nut structure configured to rotatably receive the threaded gantry rod.

The gantry translation motor may be supported on the frame.

The turntable translation assembly may include a threaded turntable rod rotatably supported on the gantry assembly, the threaded turntable rod being in threaded engagement with a nut structure of the turntable assembly; and a turntable translation motor connected to the threaded turntable rod for rotating the threaded turntable rod in a first direction and a second direction. In operation rotation of the turntable translation motor in the first direction may cause the turntable assembly to translate in a first direction; and rotation of the turntable translation motor in the second direction may cause the turntable assembly to translate in a second direction.

The turntable assembly may include a nut structure configured to rotatably receive the threaded turntable rod.

The turntable translation motor may be supported on the gantry assembly.

The gantry assembly may include a turntable rotation motor supported thereon, wherein the turntable rotation motor may be operatively connected to the turntable gear to cause the turntable gear to rotate in a first direction and a second direction.

The turntable assembly may include a carriage motor in operative communication with the carriage, wherein actuation of the carriage motor results in translation of the carriage along the rail column.

The turntable assembly may include a component holder supported on the carriage. The component holder may include a gripper having a first pair of fixed, spaced apart jaws, the first pair of jaws including a first jaw and a second jaw; and a second pair of fixed, spaced apart jaws, the second pair of jaws including a first jaw and a second jaw. The first pair of jaws may be translatable relative to the second pair of jaws. The first jaw of the first pair of jaws may be interposed between the second pair of jaws, and the second jaw of the second pair of jaws may be interposed between the first pair of jaws.

Operation of the gripper may include translation of the first pair of jaws relative to the second pair of jaws to grip a component at a first gripping position located between the first jaw of the first pair of jaws and the first jaw of the second pair of jaws; a second gripping position located between the second jaw of the first pair of jaws and the first jaw of the second pair of jaws; and a third gripping position located between the second jaw of the first pair of jaws and the second jaw of the second pair of jaws.

According to another aspect of the present disclosure, a component holder for an automatic or semi-automatic preparation system for selectively securing a vial containing one of a liquid or a non-liquid material for the formation of a medicament solution, is provided. The component holder includes a lower spur gear; a first motor in driving relation with the lower spur gear, wherein actuation of the first motor causes the component holder to rotate; an upper spur gear supported on the lower spur gear; a pair of jaws translatably supported on the upper spur gear, on a side opposite the lower spur gear, each jaw defines a V-shaped recess in juxtaposed surfaces thereof, wherein the V-shaped recess approximate toward one another as the pair of jaws translate toward one another; and a second motor is driving relation with the pair of jaws, wherein actuation of the second motor causes the pair of jaws to translate relative to one another.

A first jaw of the pair of jaws may be defined by a plurality of spaced apart walls defining a plurality of gaps; and a second jaw of the pair of jaws may be defined by a plurality of spaced apart walls defining a plurality of gaps.

In operation, upon an approximation of the pair of jaws toward one another, the walls of the first jaw may enter the gaps of the second jaw, and the walls of the second jaw may enter the gaps of the first jaw.

The walls of the first jaw may define the V-shaped recess thereof, and the walls of the second jaw may define the V-shaped recess thereof.

The first jaw may include a first grip block supported thereon, and the second jaw may include a second grip block supported thereon, wherein each grip block defines a respective V-shaped recess.

The V-shaped recess of the first grip block may be aligned with and in registration with the V-shaped recess of the first jaw, and the V-shaped recess of the second grip block may be aligned with and in registration with the V-shaped recess of the second jaw.

The component holder may further include a pair of parallel, spaced-apart rails supported on the upper spur gear, wherein the pair of jaws are translatably supported on the pair of rails.

The component holder may further include a pinion gear non-rotatably supported on a central axis of rotation of the lower spur gear, the pinion gear extending through a central axis of rotation of the upper spur gear; and a rack extending from each of the pair of jaws, wherein each rack is in meshing engagement with the pinion gear.

In operation, rotation of the lower spur gear in a first direction may rotate the pinion gear in a first direction to move the pair of jaws in a first direction relative to one another; and rotation of the lower spur gear in a second direction may rotate the pinion gear in a second direction to move the pair of jaws in a second direction relative to one another, wherein the first direction and the second direction are opposite to one another.

According to a further aspect of the present disclosure, a component holder for an automatic or semi-automatic preparation system for selectively securing a component for the formation of a medicament solution, is provided. The component holder includes a platform; a spur gear rotatably supported on the platform, the spur gear defining a central axis of rotation; a motor in driving relation with the spur gear, wherein actuation of the motor causes the component holder to rotate about the central axis of rotation; a pair of opposed jaws each pivotably supported on the spur gear, in mirrored relation across the central axis of rotation, each jaw defines a V-shaped recess in juxtaposed surfaces thereof; a pair of uprights supported on the spur gear, wherein a first upright of the pair of uprights is located adjacent a first jaw of the pair of opposed jaws on a side opposite the V-shaped recess thereof, and wherein a second upright of the pair of uprights is located adjacent a second jaw of the pair of opposed jaws on a side opposite the V-shaped recess thereof; and a biasing member disposed between each of the pair of uprights and a respective one of the pair of jaws, wherein the biasing members urge the pair of jaws towards one another.

Each of the pair of jaws may include a gear feature projecting therefrom, wherein each gear feature is in meshing engagement with one another, whereby actuation of one of the pair of jaws results in concomitant actuation of the other of the pair of jaws.

A pivot axis of each of the pair of jaws may extend perpendicularly to the central axis of rotation.

The component holder may further include a saw-tooth shaped cup slidably supported in a floor of platform, and located between the pair of jaws.

A central axis of the saw-tooth shaped cup may be aligned with the central axis of rotation.

The component holder may further include a biasing member for urging the saw-tooth shaped cup out of the platform.

The component holder may further include a shroud extending from the platform and defining a bore therein having a longitudinally extending channel formed in a surface of the bore, wherein the saw-tooth shaped cup is slidably received in the bore of the shroud, wherein the saw-tooth shaped cup includes at least one tab projecting radially from a surface thereof and which slidably resides in the channel of the shroud.

The shroud may be non-rotatably secured to the spur gear.

The invention will be explained in greater detail below in descriptions of preferred embodiments and referring to the attached figures.

BRIEF DESCRIPTION OF THE DRAWINGS

In the following, the preferred embodiments of invention will be described in detail with reference to the following attached figures.

DETAILED DESCRIPTION

Figure 1:
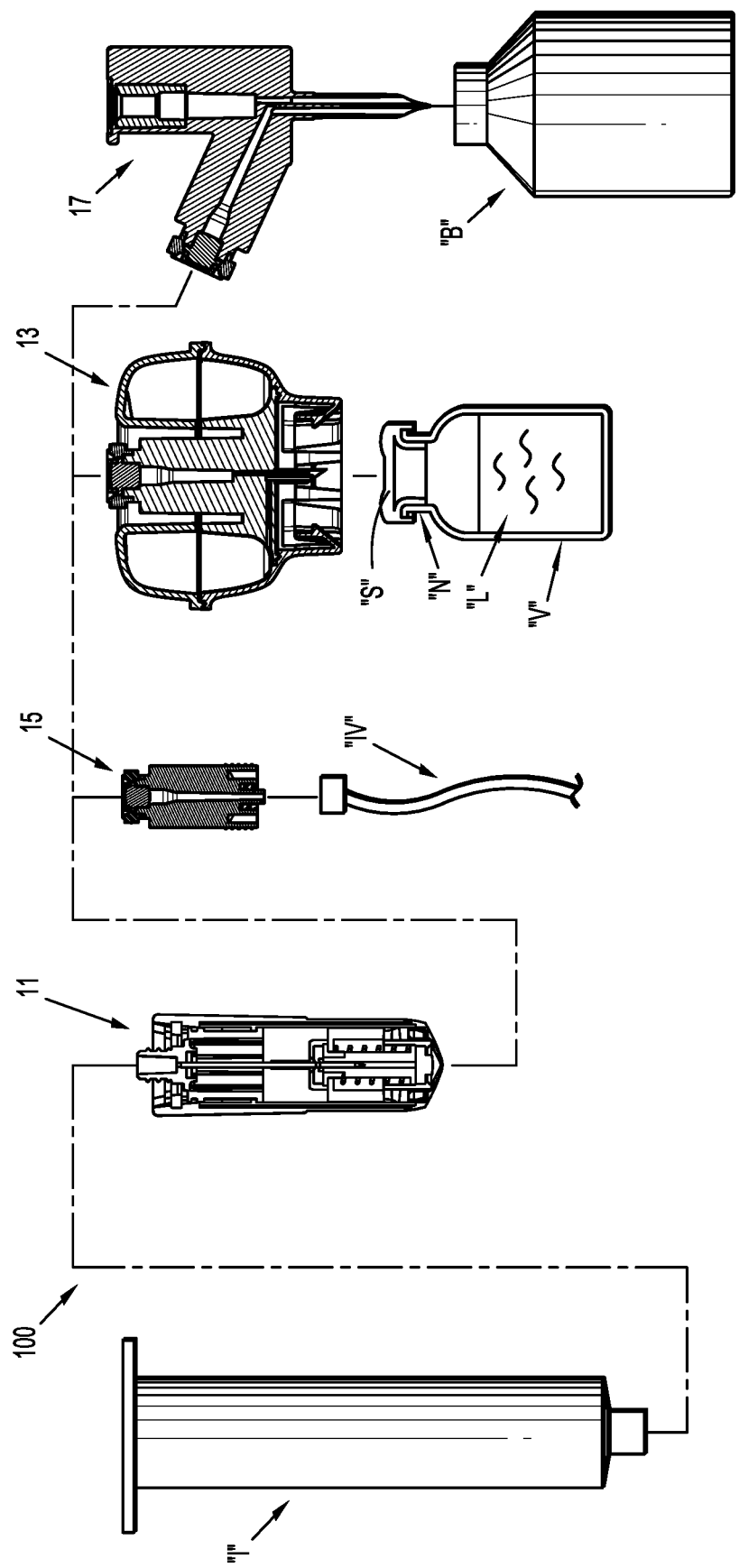
FIG. 1 is a schematic illustration of a closed fluid transfer system, according to the prior art, illustrating a fluid connectability of a syringe to an I.V. Set, a vial and an I.V. bag via combination of a syringe adapter and one of an I.V. set adapter, a vial adapter and an I.V. bag adapter.

With reference to FIGS. 1-13, a closed fluid transfer system, according to the prior art, is generally designated as 100 and generally includes a module/adapter that fluidly connects to a syringe or any male luer lock connection point; a patient push module/adapter that fluidly connects directly to an I.V. line; at least a module/adapter that fluidly connects to a vial/container storing/containing a fluid/liquid in the form of a hazardous drug and the like; and a module/adapter that fluidly connects to an I.V. bag. Each of the above-mentioned modules/adapters will be described in greater detail below with reference to the accompanying figures, wherein like numbers identify like elements.

The system is a "closed" fluid-transfer system capable of transferring liquids between a conventional syringe and one of a patient I.V. set, a vial, or an I.V. bag without leaking or spilling and without exposure of the gases/fluids/liquids or other substances to a location or a substance outside the closed system. One purpose of the closed fluid transfer system is to permit health care personnel to safely use and handle liquid-form medicine, including potentially hazardous liquid drugs and/or the like.

The closed fluid transfer system 100 includes a syringe adapter 11 (see FIGS. 1-4) that is structured to provide a closed fluid connection between a first fluid container in the form of a conventional needleless syringe "I" and a second fluid container/conduit in the form of a patient I.V. set, a vial "V", or an I.V. bag. The fluid transfer is accomplished by first connecting one of a patient push adapter 15 (see FIGS. 1 and 8-11) to an I.V. set, a vial adapter 13 (see FIGS. 1 and 5-7) to a vial, or an I.V. bag adapter 17 (see FIGS. 1 and 12-13) to an I.V. bag, as necessary. Each adapter 13, 15, 17 is provided with an identical male stem 19 which defines an internal lumen 21 closed at one end by a resilient seal 23. The syringe adapter 11 is mated to the male stem 19, thereby permitting fluid flow from or to the syringe "I".

Referring now specifically to FIGS. 1-7, the closed fluid transfer system 100 includes a syringe adapter 11. Syringe adapter 11 is a type of valve which can be in an open state to permit fluid flow therethrough or in a closed state to prevent fluid flow. The open and closed states occur in a specific sequence dictated by the syringe adapter 11.

The syringe adapter 11 consists of four main parts which are a housing 25, a conventional hollow metal needle 27, a shuttle 29, and a collar 31. The housing 25 is generally cylindrical in shape having a distal end 33 and a proximal end 35, a longitudinal axis 37, a distal opening 39, and a female cavity 41 into which the male stem 19 is received. Housing 25 may be formed to have two housing side portions or halves 43, 45 and a housing base portion 47 which fits partially between the side portions 43, 45. Side portions 43, 45 define opposed slots 49, 51 (see FIGS. 2 and 4) which begin at housing distal end 33 and extend within housing 25. Slots 49, 51 which receive a respective guide pin 53, 55 and guide surface 57, 59 of any male stem 19, which are each keyed to a respective one of the slots 49, 51 (or a respective one of slots 51, 49), for the purposes described in full detail below.

Figure 3:
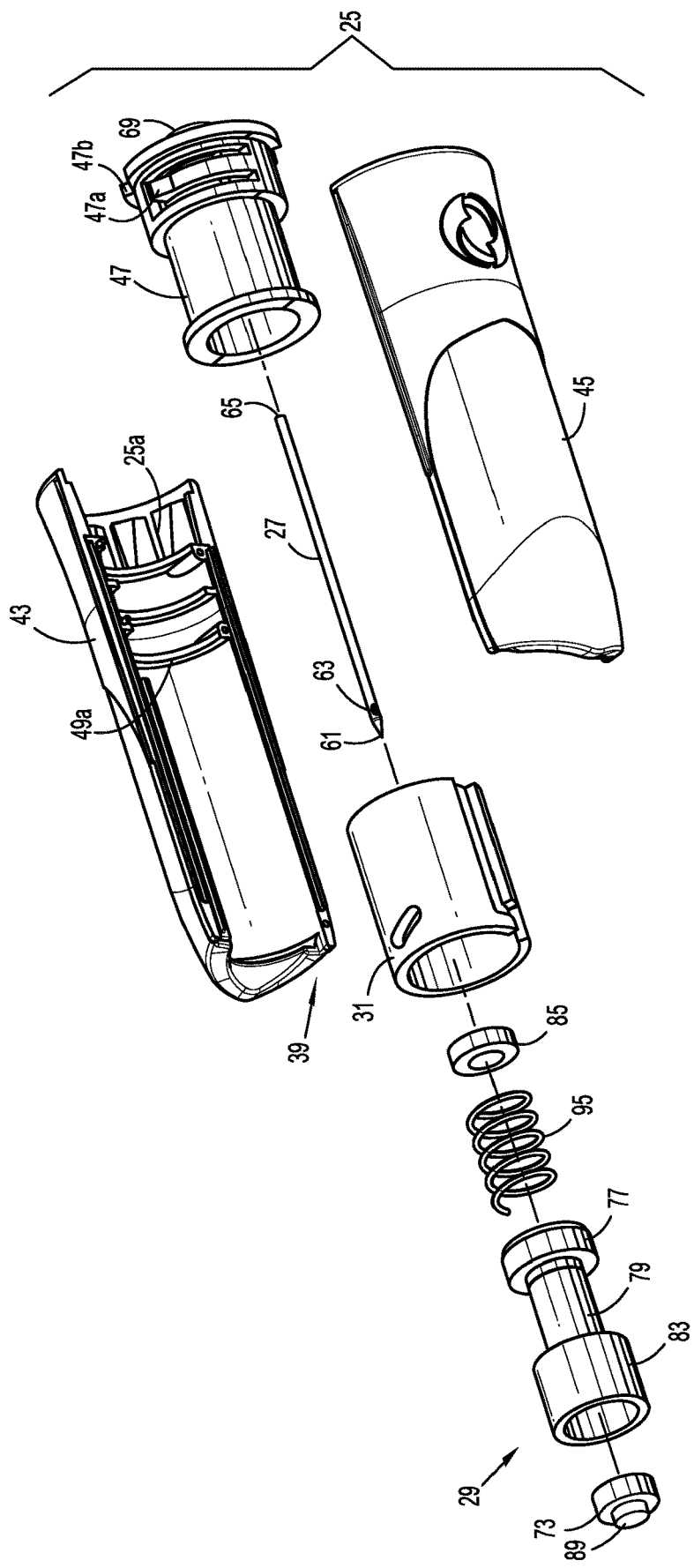
FIG. 3 is a perspective view, with parts separated, of the prior art syringe adapter of FIG. 2.
Figure 4:
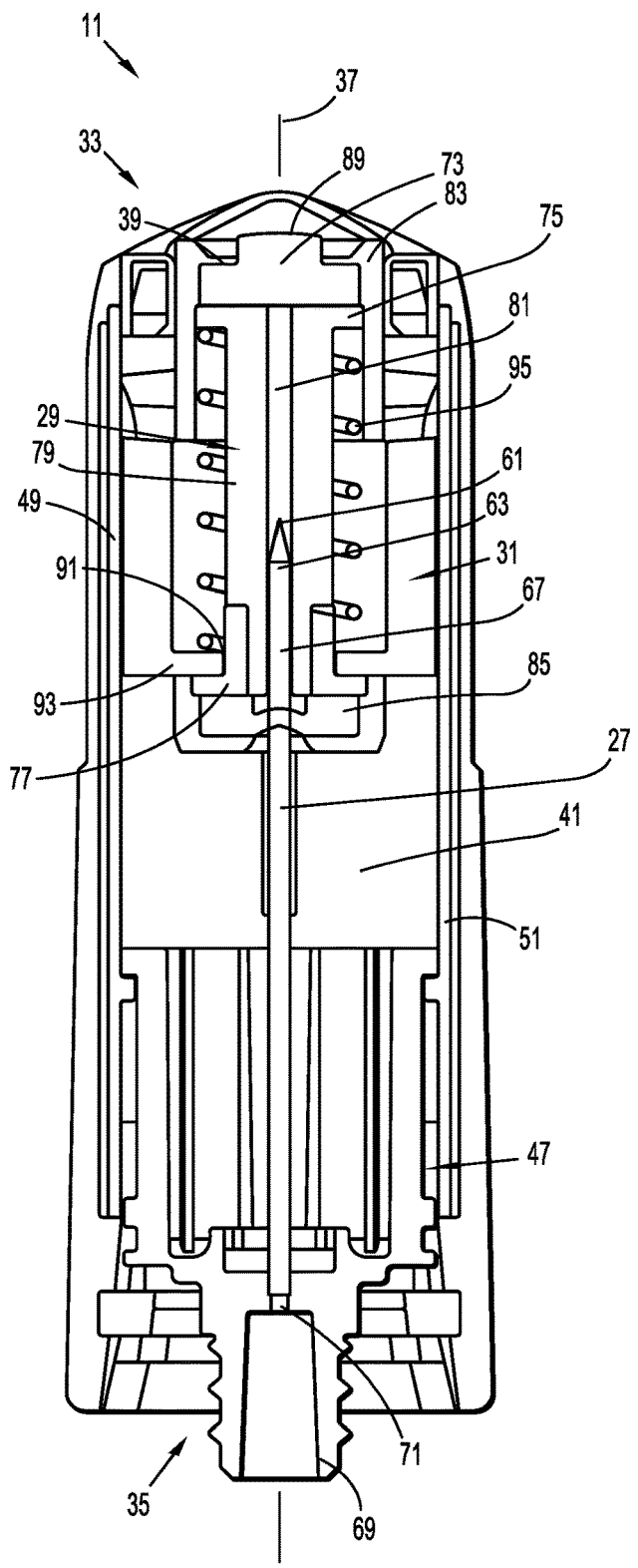
FIG. 4 is a longitudinal, cross-sectional view of the prior art syringe adapter of FIGS. 2 and 3.

Hollow metal needle 27, as seen in FIGS. 3 and 4, is a conventional needle with a sharpened tip 61, a tip end opening 63, a proximal end opening 65, and a lumen 67 permitting fluid flow through the conventional needle 27 between the needle openings 63, 65. It is envisioned that needle 27 will be a conventional 18 gauge steel "pencil tip" needle commercially available (18 gauge refers to the outer diameter of needle 27). The conventional pencil tip needle 27 has an extremely sharp tip 61 with opening 63 spaced slightly away from the sharpened tip 61. The pencil tip needle 27 is of a type and size conventionally used with syringes to penetrate patient blood vessels for delivery or extraction of fluids.

Needle 27 is mounted within housing 25, in fixed-positional relationship, on an inner side of base 47 with tip 61 of needle 27 pointing/extending toward distal end 33 of housing 25. An advantage of this design is that needle 27, and specifically, the extremely sharp needle tip 61 of needle 27, are fully enclosed within the housing 25 and are completely shielded from contact with a user. In this manner, the possibility of injuries as a result of user needle-stick, has been significantly reduced and/or eliminated.

Housing base 47 is rotatably supported in housing 25. Housing base 47 includes an outer side with a conventional luer connector 69 provided to accept the delivery end of a conventional needless syringe. A lumen 71 extends through base 47 between luer connector 69 and proximal opening 65 of needle 27 permitting fluid flow between the needle tip opening 63 and the luer connector 69.

Housing 25 and housing base 47 of syringe adapter 11 cooperate with one another to provide a ratchet mechanism by which syringe adapter 11 may not be accidentally or inadvertently disconnected from syringe "I". In particular, the ratchet mechanism includes, as seen in FIG. 3, a plurality of ribs 25a formed on an inner surface of housing 25 and at least one resilient finger 47a supported on housing base 47, whereby housing base 47 is held in a fixed position relative to housing 25 when syringe adapter 11 is connected to syringe 11 and to is free to rotate relative to housing 25 if syringe adapter 11 is being inadvertently or accidently disconnected from syringe "I". In this manner, the closed system between the syringe adapter 11 and syringe 11 is better maintained.

Generally, in operation, when syringe adapter 11 is connected to syringe "I", the at least one resilient finger 47a of housing base 47 engages ribs 25a of housing in such a manner that rotation of housing base 47 relative to housing 25 is inhibited and syringe adapter 11 may be securely connected to syringe "I". Further, if there is an inadvertent or accidental rotation of syringe adapter 11 relative to syringe "I", tending to disconnect syringe adapter 11 from syringe "I", and thus destroy the closed system, each resilient finger 47a is configured to slip over and across ribs 25a of housing 25, allowing housing base 47 to rotate relative to housing 25 and thus maintain the closed system.

If it is desired to intentionally disconnect syringe "I" from syringe adapter 11, a user may squeeze housing 25 radially inward, in the proximity of luer connector 69, to engage at least one tooth (not shown) formed on an inner surface of housing 25 with a respective notch 47b formed in an outer surface of housing base 47. Then, with the at least one tooth (not shown) of housing 25 engaged with the respective notch 47b of housing base 47, the user may rotate syringe adapter 11 relative to syringe "I" to disconnect syringe "I" from luer connector 69 of housing base 47.

Shuttle 29 is provided for at least the following important purposes. First, shuttle 29 supports shuttle distal seal 73 across distal opening 39 of housing 25 to close cavity 41 of housing 25 so that contaminants cannot enter the housing 25 when the syringe adapter 11 is not mated to one of the adapters 13, 15, 17. Second, the shuttle 29 supports shuttle distal seal 73 at a position across distal opening 39 of housing 25 so that distal seal 73 can be easily swabbed with alcohol before use to ensure that the seal 73 is sterile. In accordance with the present disclosure, and as is customary, a seal 23 of any male stem 19 (as seen in for example FIG. 5 and as will be described in greater detail below) is also swabbed with alcohol or other microbial agent before being mated to the syringe adapter 11, so as to ensure sterility of the abutment between seals 23 and 73. Finally, the shuttle 29 provides a fluid-tight enclosure for needle 27 to prevent fluid flow outside of syringe adapter 11 when in the closed state.

As illustrated in FIGS. 3 and 4, shuttle 29 includes distal and proximal annular flanges 75, 77, respectively, and an intermediate body portion 79 between flanges 75, 77 defining a shuttle lumen 81 therethrough. Distal flange 75 supports a distal seal 73 and a barrel 83, seated on distal flange 75, holds distal seal 73 on distal flange 75. Shuttle proximal flange 77 supports a proximal seal 85.

As illustrated in FIGS. 3 and 4, tip 61 of needle 27 extends into shuttle lumen 81 and proximal seal 85 forms a fluid-tight seal around needle 27. In the closed state, when syringe adapter 11 is fluidly connected to syringe "I", needle tip 61 and opening 63 are within shuttle lumen 81 and seals 73, 85 prevent fluid from exiting shuttle lumen 81.

Each seal 23, 73 is generally disk shaped and includes a respective outward projection 87, 89 (i.e., convex surface) which abut one another when the seals 23, 73 are held together, as described later herein. Seals 23, 73 and 85 are made of polyisoprene and seals 23 and 73 are designed want to retain or return to their original convex profile when in abutment with one another. Put another way, since seals 23, 73 are fabricated from a resilient material and tend to want to retain or return to their original convex profile, when seals 23, 73 are in abutment with one another, a substantially continuous interface between seals 23, 73 is established and maintained. While it is preferred that seals 23 and 73 be made from polyisoprene, it is contemplated and within the scope of the present disclosure, that seals 23, 73 may be made from thermoplastic elastomers (TPE), silicone, more specifically, HaloButyl-Polyisoprene, Chlorobutyl, thermoplastic vulcanizates (TPVs), any other resilient polymer, or any combinations thereof.

Intermediate portion 79 of shuttle 29 rides in collar opening 91 in collar end wall 93 of collar 31 for axial movement along axis 37 within housing 25. Barrel 83 is generally cylindrical in shape and has an outside diameter slightly less than an inside diameter of collar 31 to permit barrel 83 and shuttle 29 to reciprocate inside collar 31.

A spring 95 is provided and bears against end wall 93 of collar 31 and distal flange 75, partially within barrel 83. Spring 95 biases shuttle 29 toward distal end 33 of housing 25 so that distal seal 73 of shuttle 29 covers or extends across opening 39 of housing 25, for the reasons previously described. Spring-biased contact between barrel 83 and end wall 93 of collar 31 limits inward movement of shuttle 29 toward proximal end 35 of housing 25, and contact between proximal flange 77 of shuttle 29 and end wall 93 of collar 31 limits outward movement of shuttle 29 toward distal end 33 of housing 25.

Distal seal 73 of shuttle 29 does not contact the housing 25 and is supported solely by shuttle 29 and travels within collar 31 spaced from housing 25. Shuttle 29 is pushed axially toward proximal end 35 of housing 25 when contacted by seal 23 of any male stem 19 during use, as described more fully below.

Figure 2:
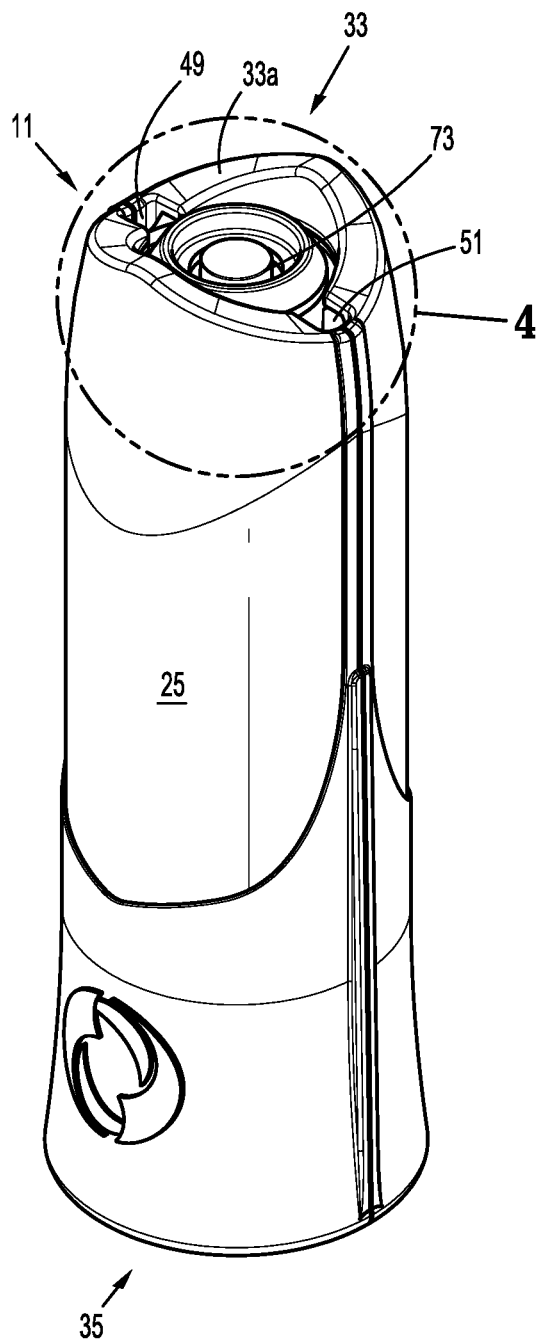
FIG. 2 is a perspective view of a prior art syringe adapter of the closed fluid transfer system of FIG. 1.
Figure 8:
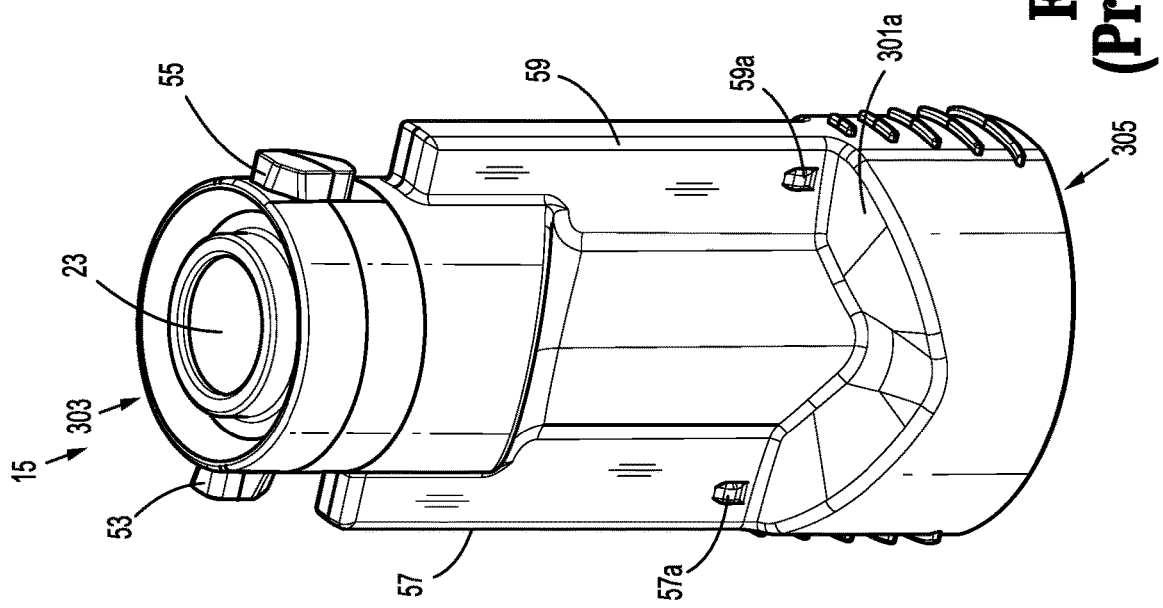
FIG. 8 is a top, perspective view of a prior art patient push adapter of the closed fluid transfer system of FIG. 1.

With continued reference to FIGS. 2-4, collar 31 and housing 25 cooperate to hold male stem 19 and seal 23 (for example, as seen in FIG. 8) thereof in abutment with distal seal 73 of shuttle 29 so that the abutting seals 23, 73 can subsequently be pierced by needle tip 61 of needle 27 and so that needle 27 can enter lumen 21 of male stem 19 to open the fluid path through syringe adapter 11. The abutment between seals 23, 73 established that distal seal 73 of shuttle 29 is the closure for distal opening 39 of housing 25 and also places distal seal 73 of shuttle 29 in a position convenient for swabbing with alcohol before use. The abutment between seals 23, 73 ensures that the two seals 23, 73 function as one and can be pierced together by needle 27. If the seals 23, 73 were to separate with needle tip opening 63 extended outside of lumen 81 of shuttle 29, liquids could leak into cavity 41 of housing 25, which is contrary to the purpose of providing a closed system.

Referring now to FIGS. 3-4, collar 31 is generally cylindrical in shape corresponding to the shape of cavity 41 of housing 25. Collar 31 includes a proximal end wall 93 and a side wall 97 extending from proximal wall 93.

Turning now to FIGS. 1 and 5-7, vial adapter 13 of the closed fluid transfer system 100 will be discussed in greater detail. Generally, vial adapter 13 connects to a neck "N" of a vial, bottle, or other container "V" holding liquid "L" to be extracted or into which liquid is to be delivered. For convenience, these containers will be referred to collectively by the term "vial." Vial adapter 13 may be provided in sizes and configurations as necessary to attach to commercially-available vials.

Figure 5:
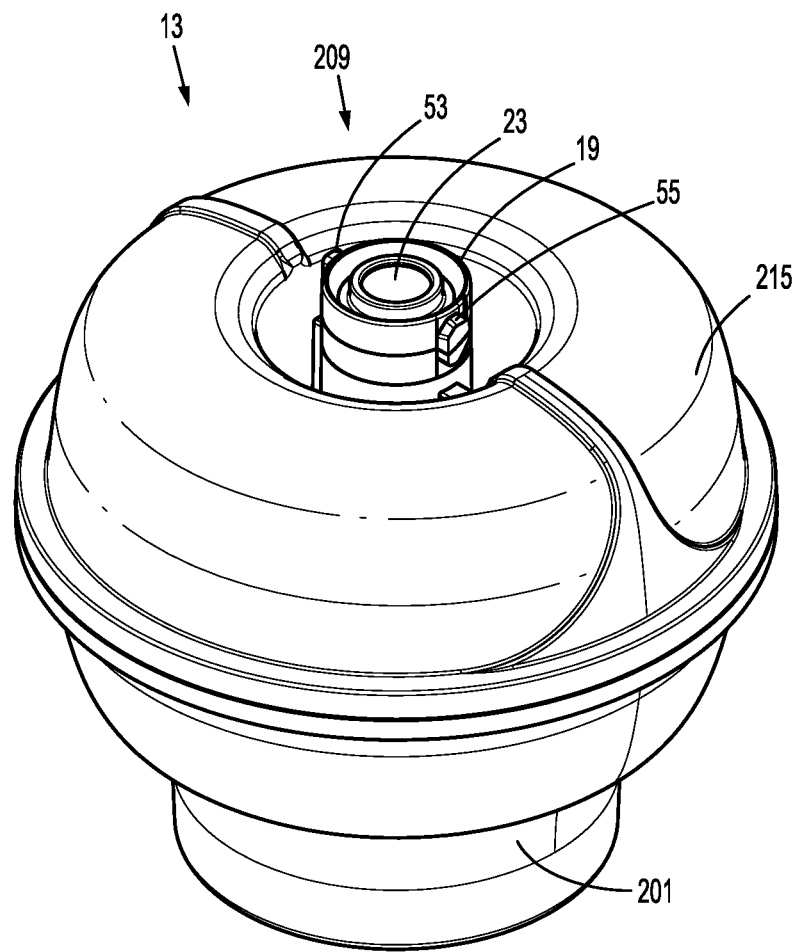
FIG. 5 is a perspective view of a prior art vial adapter of the closed fluid transfer system of FIG. 1.
Figure 6:
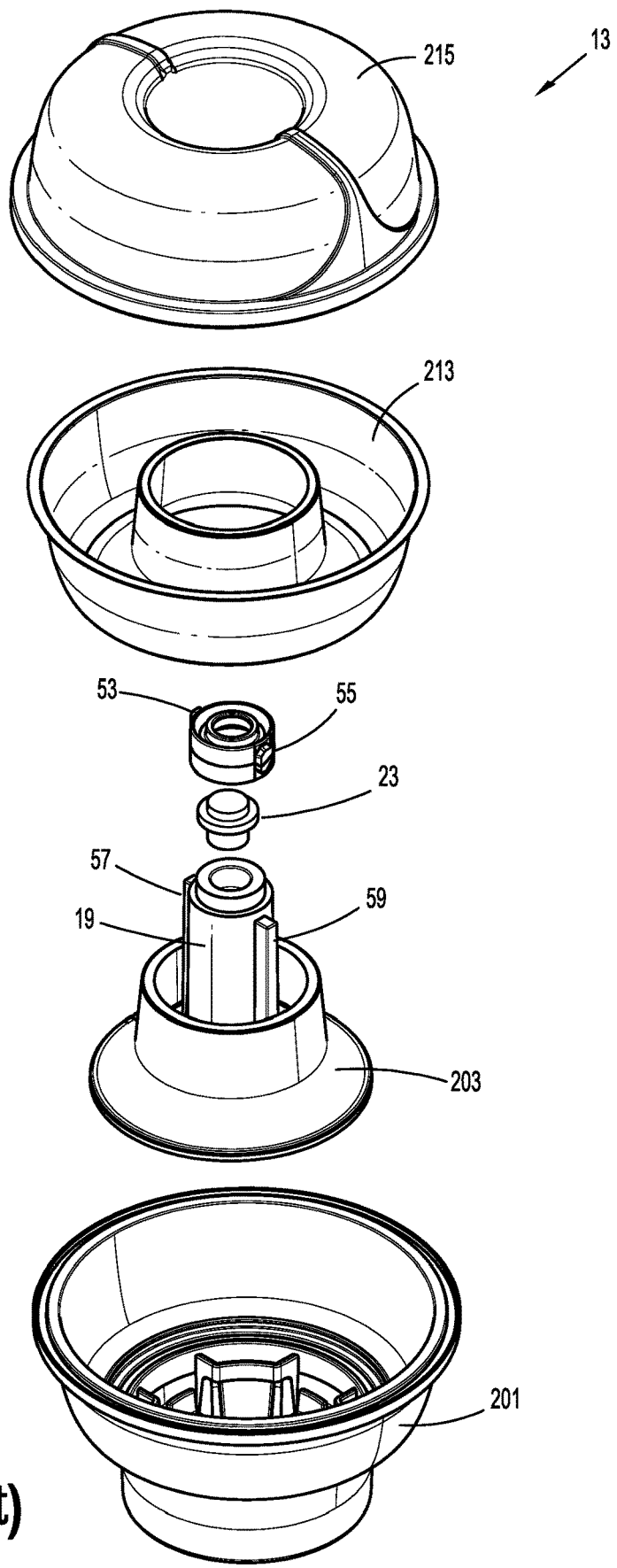
FIG. 6 is a perspective view, with parts separated, of the prior art vial adapter of FIG. 5.
Figure 7:
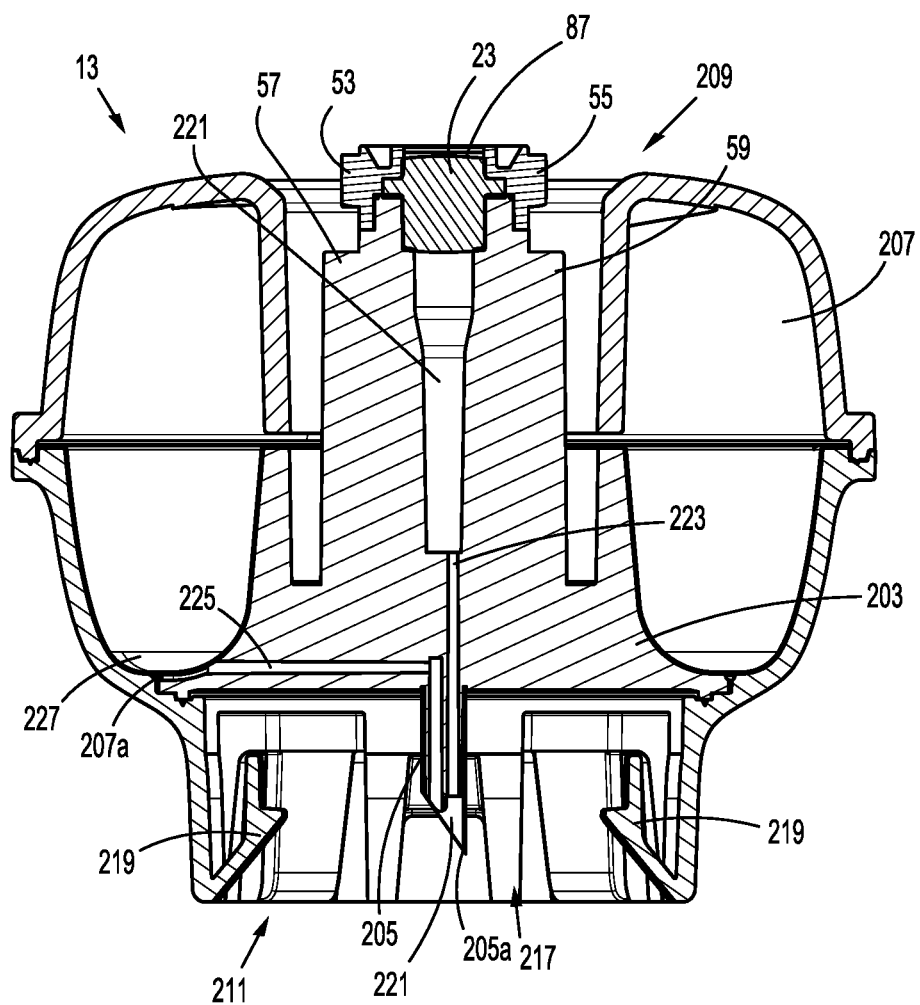
FIG. 7 is a longitudinal, cross-sectional view of the prior art vial adapter of FIGS. 5 and 6.

As illustrated in FIGS. 5-7, vial adapter 13 includes a base 201, an adapter support 203 (including a male stem 19 supporting a seal 23 and including guide pins 53, 55, as described above), a spike 205, and an expansion chamber 207. Vial adapter 13 includes distal and proximal ends 209, 211.

As best shown in FIGS. 6 and 7, base 201 is substantially bowl-shaped and is configured to receive and/or seat an adapter support 203 thereon. Vial adapter 13 includes a toroid-shaped expansion chamber 207, including a bladder 227 and translucent cover 215, seated on an inner rim and an outer rim of base 201. Bladder 227 having a substantially U-shaped radial cross-section including a first annular rim captured between the outer annular rim of base 201 and the outer annular rim of cover 215, and a second annular rim captured between the inner annular rim of base 201 and the inner annular rim of cover 215.

Base 201 of vial adapter 13 includes a circular opening 217 along proximal end 211 thereof into which neck "N" of vial "V" is received. Retainers 219 are provided around the circumference of opening 217 to connect base 201 of vial adapter 13 to form a permanent connection once the neck "N" of the vial "V" is inserted into opening 217.

As seen in FIG. 7, spike 205 extends away from proximal end 211 of base 201 and includes a tip 221 configured to pierce a septum "S" provided on vial "V" when the neck "N" of the vial "V" is inserted into opening 217 of base 201. Spike 205 has a length sufficient to extend into the vial "V". Spike 205 is preferably made of plastic, however, it is envisioned that spike 205 may preferably support a metallic piercing member or hypo-tube 205a to assist in the ability of spike 205 to penetrate the septum "S" of the vial "V".

As seen in FIG. 7, spike 205 and adapter support 203 define two ducts 223, 225. A first duct 223 extends between tip 221 of spike 205 and lumen 21 of male stem 19, and is provided to permit fluid flow between the vial "V" and male stem 19. As described above, opening 63 of tip 61 of needle 27 extends into lumen 21 to extract or deliver liquid through duct 223 when syringe adapter 11 is in the open state. A second duct 225 extends between tip 221 of spike 205 and a first cavity 207a of chamber 207 defined within expansion chamber 207 when toroid-shaped bladder 227 is deflated. Chamber 207a of expansion chamber 207 expands upon a movement of bladder 227 when air or other gas is injected into male stem 19 and duct 223 from a syringe "I" that is attached to syringe adapter 11.

Turning now to FIGS. 1 and 8-11, patient push adapter 15 of the closed fluid transfer system 100 will be discussed in greater detail. In general, patient push adapter 15 connects to tubing of a patient I.V. set permitting delivery of liquids directly to the patient from a syringe "I" attached to the patient push adapter 15.

The patient push adapter 15 includes a body 301 having respective distal and proximal ends 303, 305. Body 301 of patient push adapter 15 is preferably a one-piece molded plastic part. Distal end 303 of patient push adapter 15 includes a male stem 19 defining a lumen 21, having a seal 23 supported across lumen 21, having guide pins 53, 55 projecting radially outward from on outer surface thereof, and having guide surfaces 57, 59 projecting radially outward from on outer surface thereof. Proximal end 305 of patient push adapter 15 includes a conventional luer connector 307 configured to accept a mating luer connector of a patient I.V. set "IV" (see FIG. 1). Lumen 21 extends through body 301, between seal 23 and luer connector 307, permitting fluid flow between the opening 63 of tip 61 of needle 27 and the luer connector 307, when patient push adapter 15 is properly connected to syringe adapter 11, as described above.

Figure 9:
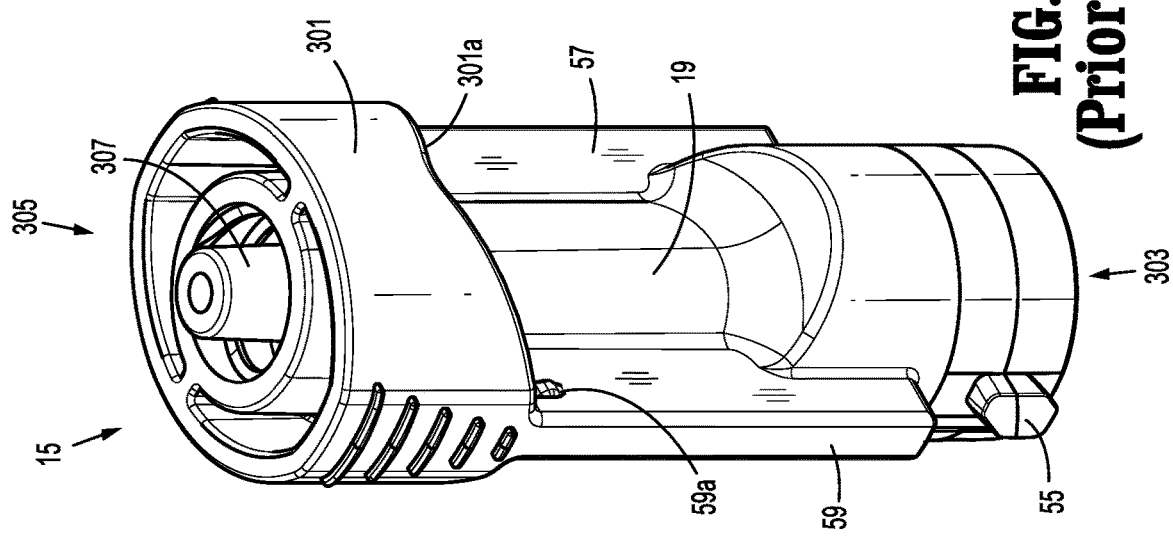
FIG. 9 is a bottom, perspective view of the prior art patient push adapter of the closed fluid transfer system of FIG. 1.
Figure 10:
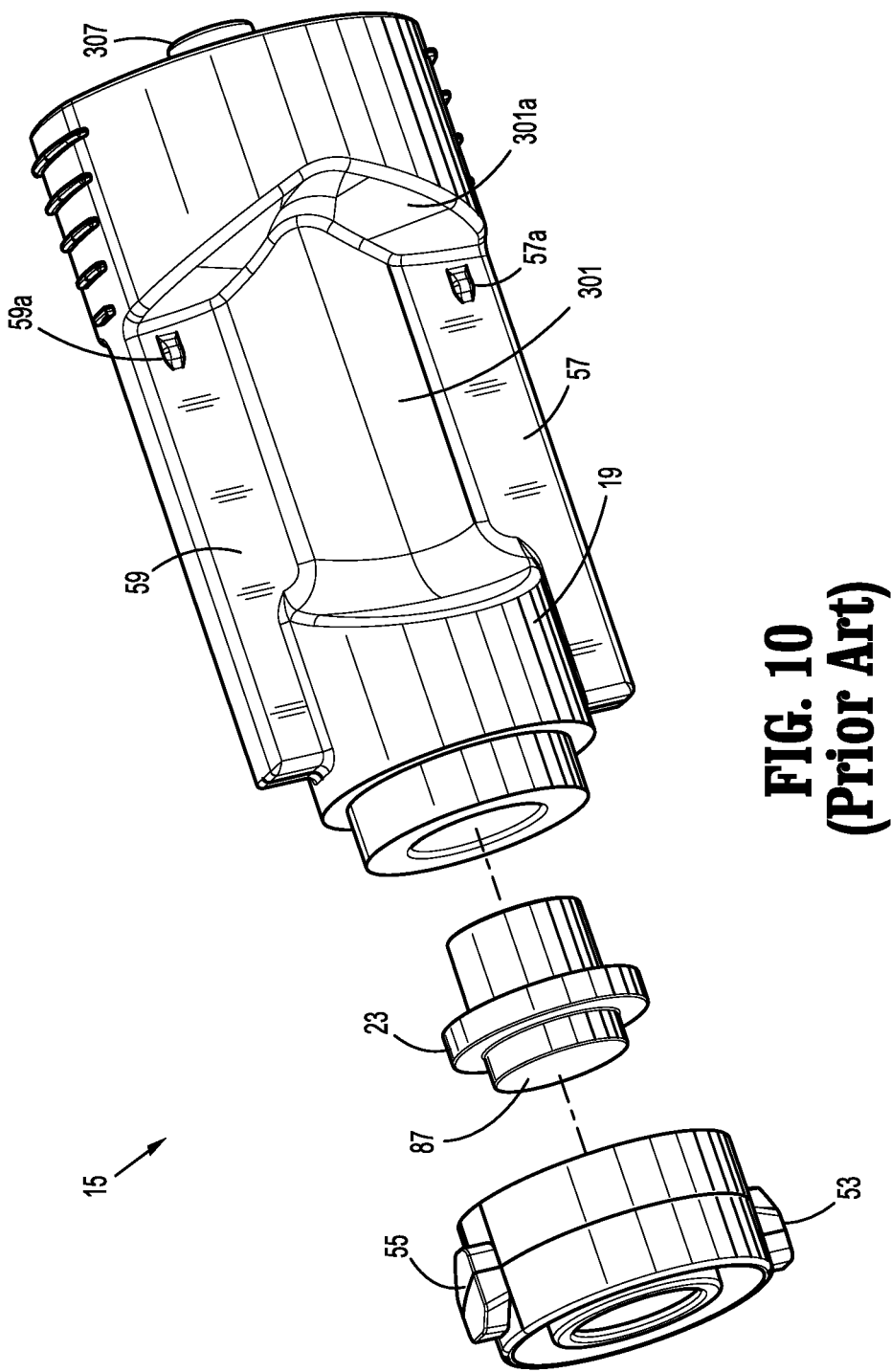
FIG. 10, is a perspective view, with parts separated, of the prior art patient push adapter of FIGS. 8 and 9.
Figure 11:
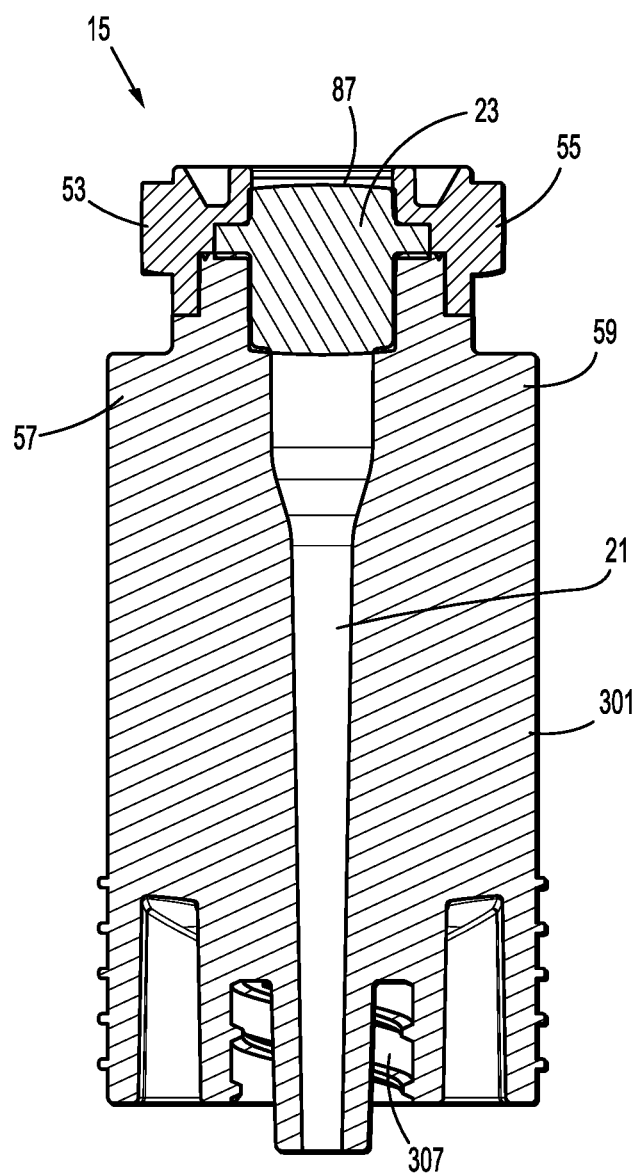
FIG. 11 is a longitudinal, cross-sectional view of the prior art patient push adapter of FIGS. 8-10.

With reference to FIGS. 8-10, it is contemplated that at least one nub 57a, 59a may project from a surface of respective guide surfaces 57, 59 of patient push adapter 15 and which are configured to snap-fit engage respective complementary detents or recesses defined in slots 49, 51 of syringe adapter 11, or more particularly, an appropriately sized annular rib 49a (see FIG. 3) formed in an inner surface of halves 43, 45 of housing 25 of syringe adapter 11. The interaction of nubs 57a, 59a, and complementary detents or recesses defined in slots 49, 51 or annular rib 49a (see FIGS. 3 and 4) of syringe adapter 11 provide a user with audible and/or tactile feedback that patient push adapter 15 and syringe adapter 11 are properly and fully connected to one another.

Guide surfaces 57, 59 of patient push adapter 15 provide a convenient and comfortable surface for a user to grip patient push adapter 15 and to rotate patient push adapter 15 relative to a conventional luer of I.V. set.

Figure 12:
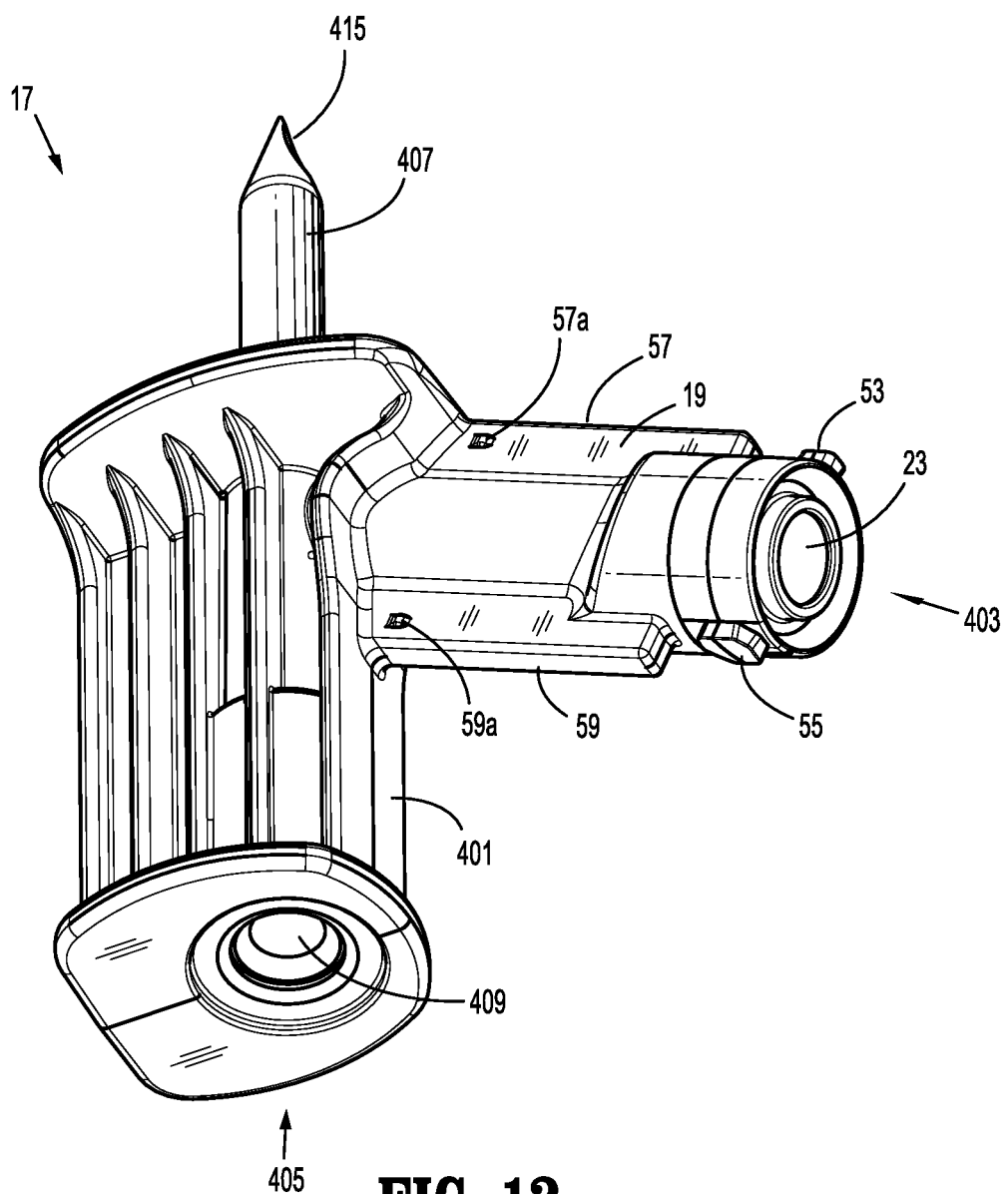
FIG. 12 is a bottom, perspective view of a prior art I.V. bag adapter of the closed fluid transfer system of FIG. 1.
Figure 13:
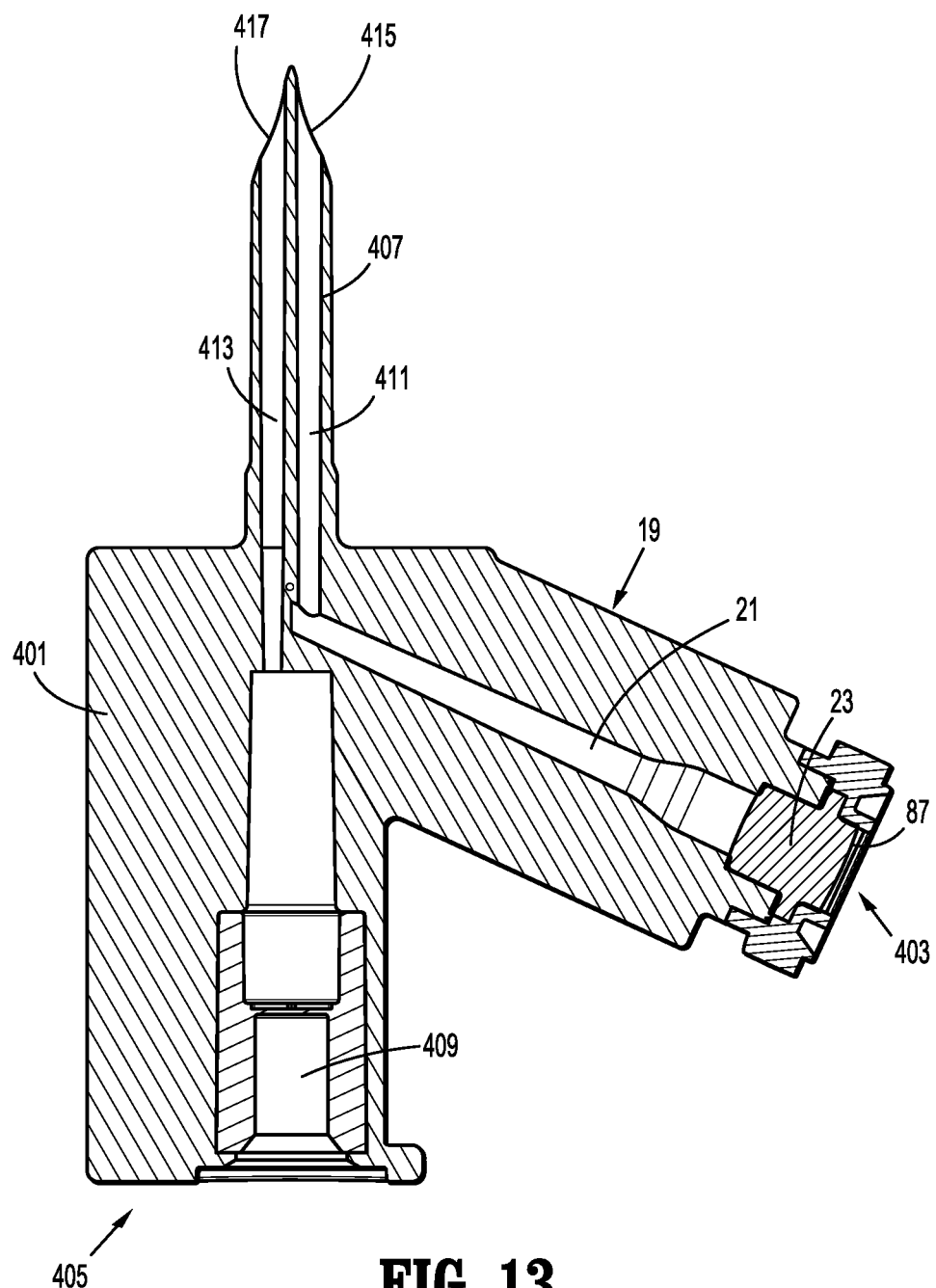
FIG. 13 is a longitudinal, cross-sectional view of the prior art I.V. bag adapter of FIG. 12.

Turning now to FIGS. 1 and 12-13, I.V. bag adapter 17 of the closed fluid transfer system 100 of the present disclosure, will be discussed in greater detail. In general, the I.V. bag adapter 17 enables liquid to be delivered to, or extracted from, a conventional I.V. bag "B" (see FIG. 1). The I.V. bag adapter 17 could also be used as a source of ventilation, permitting air to be delivered from a syringe "I" or other source into the I.V. bag to more rapidly drain the I.V. bag "B" of its liquid contents.

The I.V. bag adapter 17 includes a body 401 having respective distal and proximal ends 403, 405, and a spike 407 extending from body 401. Distal end 403 of I.V. bag adapter 17 includes a male stem 19 defining a lumen 21, having a seal 23 supported across lumen 21, having guide pins 51, 53 projecting radially outward from on outer surface thereof, and having guide surfaces 57, 59 projecting radially outward from on outer surface thereof. Body 401 of I.V. bag adapter 17 is preferably a one-piece molded plastic part. Proximal end 405 of body I.V. bag adapter 17 includes a conventional port 409 which receives a conventional tapered male connector (not shown) of a conventional infusion chamber (not shown) into which liquid drips from the I.V. bag "B". Spike 407 is tapered between distal and proximal ends 403, 405 for insertion into a conventional port (not shown) of I.V. bag "B".

Body 401 of I.V. bag adapter 17 includes two ducts 411, 413. First duct 411 is essentially an extension of lumen 21 through spike 407 extending to an opening 415 in spike 407 which would be within I.V. bag "B" when I.V. bag adapter 17 is attached to the I.V. bag "B". Second duct 413 extends between a second opening 417 in spike 407 and a port 409 for attachment to the infusion chamber (not shown). As described above, opening 63 of tip 61 of needle 27 extends into lumen 21 of male stem 19, when I.V. bag adapter 17 is properly connected to syringe adapter 11, to extract or deliver liquid (or gas) through duct 411 while syringe adapter 11 is in the open state.

In accordance with the present disclosure, a component other than a syringe adapter 11 could be connected to male stem 19 of I.V. bag adapter 17 to deliver gas to I.V. bag "B". Liquid medication delivered through duct 411 may be mixed with the contents of the I.V. bag "B". The liquid in the I.V. bag "B" may then exit the I.V. bag "B" through port 409 and into the infusion chamber for delivery to the patient.

Figure 15:
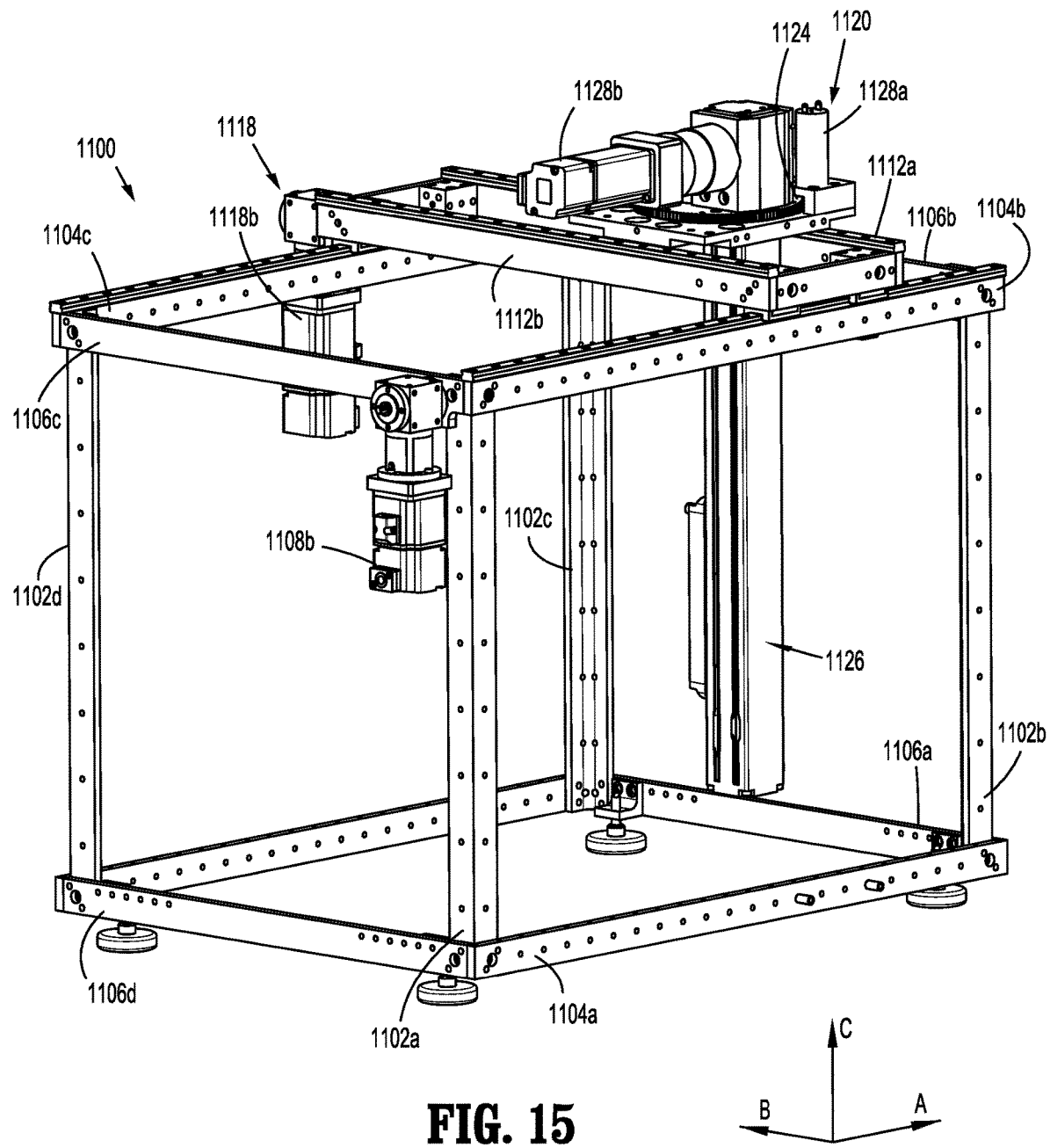
FIG. 15 is a first, perspective view of the preparation system of FIG. 14, with components removed therefrom.

With reference to FIGS. 12 and 15, it is contemplated that at least one nub 57a, 59a may project from a surface of respective guide surfaces 57, 59 of I.V. bag adapter 17 and which are configured to snap-fit engage respective complementary detents or recesses defined in slots 49, 51 of syringe adapter 11, or more particularly, an appropriately sized annular channel 49a (see FIG. 3) formed in an inner surface of halves 43, 45 of housing 25 of syringe adapter 11. The interaction of nubs 57a, 59a and complementary detents or recesses defined in slots 49, 51 or annular rib 49a (see FIGS. 3 and 4) of syringe adapter 11 provide a user with audible and/or tactile feedback that I.V. bag adapter 17 and syringe adapter 11 are properly and fully connected to one another.

For a detailed description of the construction and operation of closed fluid transfer system 100 including a syringe adapter 11, a vial adapter 13, a patient push adapter 15, an I.V. bag adapter 17, reference may be made to U.S. Pat. No. 9,107,809, the entire content of which is incorporated herein by reference.

Turning now to FIGS. 14-26, in accordance with the present disclosure, a preparation system 1000 for automatically or semi-automatically preparing hazardous medicines using syringes, vials, I.V. sets, and I.V bags of the present disclosure, is provided and set forth below.

Figure 14:
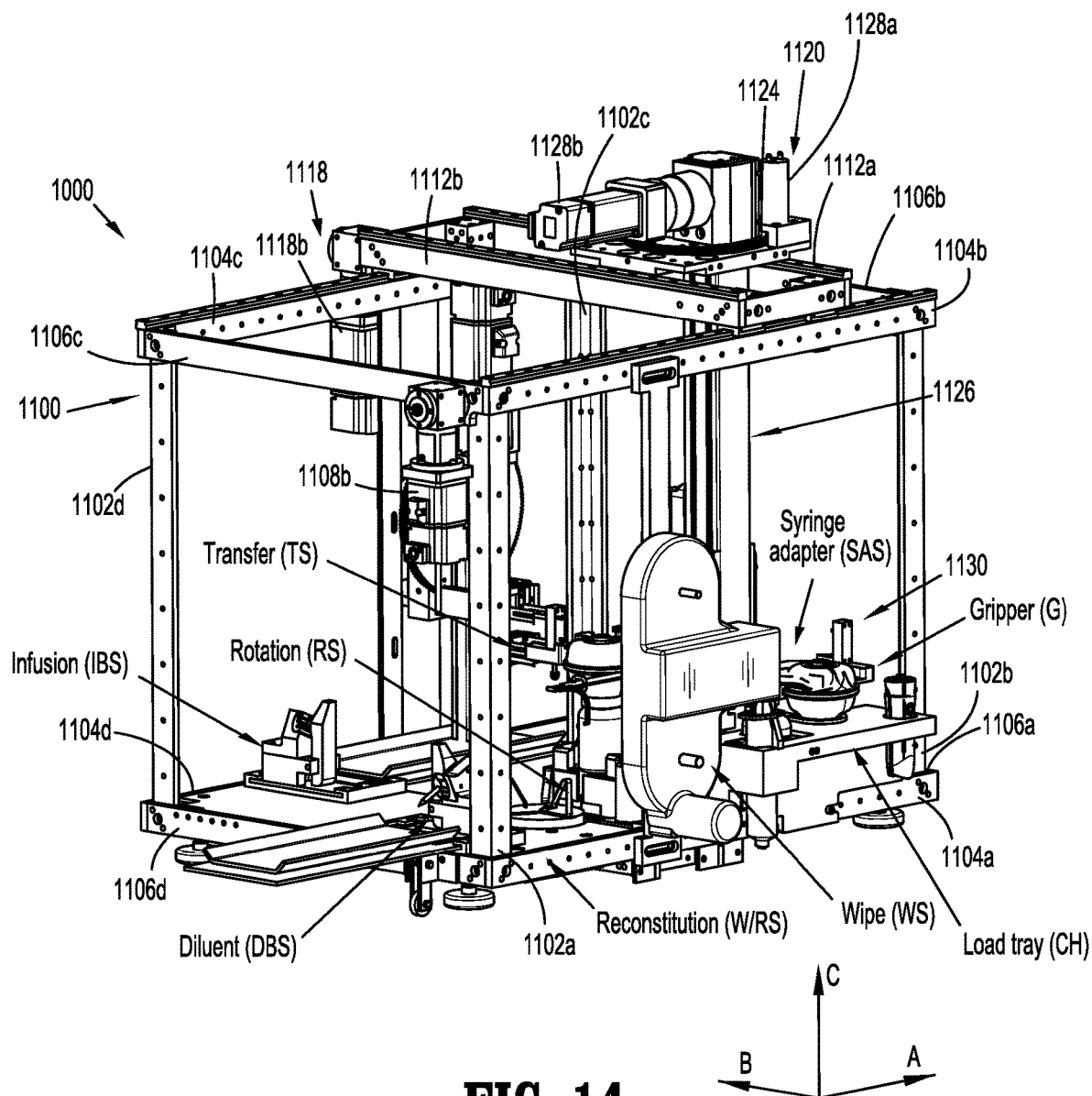
FIG. 14 is a perspective view of a preparation system according to an embodiment of the present disclosure.

Preparation system 1000 includes, as seen in FIG. 14, at least the following sub-systems and/or stations, namely, at least one gripper (G), a component holder or load tray (CH), a rotation station (RS), a syringe adapter station (SAS), a weigh or reconstitution station (W/RS), an infusion bag station (IBS), a diluent bag station (DBS), a wipe station (WS), and a transfer station (TS). Preparation system 1000 may be considered a Closed System Transfer Device (CSTD).

The Closed System Transfer Device (CSTD) of the present disclosure, has been produced for the safe transfer of potentially hazardous drugs used in the compounding of cancer treatments. The CSTD provides a means to make drug transfers between vials, syringes and IV bags without exposing the health care provider to the drug.

Early concepts for the CSTD included the possibility of applying the CSTD technology to an automated/robotic application. In this application, the CSTD, vials, syringes, etc. would be introduced to a standard pharmaceutical hood, then an automatic or semi-automatic preparation system would provide the motion, mixing, etc. required to develop a suitable drug for administration to a patient. The primary objective of such an approach would be the reliability, accuracy and repeatability afforded by an automated or semi-automated method. Further, the preparation system could be applied to multi-hood environments, improving throughput, and reducing the need for additional personnel, in particular physicians and pharmacologists to scrub and suit up.

Preparation system 1000 is intended to operate with the confines of an engineering control, e.g., a Class 2 A II BSC (hood). A characteristic of this type of hood is the provision of air flow vertically downward, emanating from HEPA filters mounted in the ceiling. Preparation system 1000 is construction and arranged to maximize or establish 'firstair' flow across each of the stations thereof, e.g., mating, surfaces of each of the components.

Figure 16:
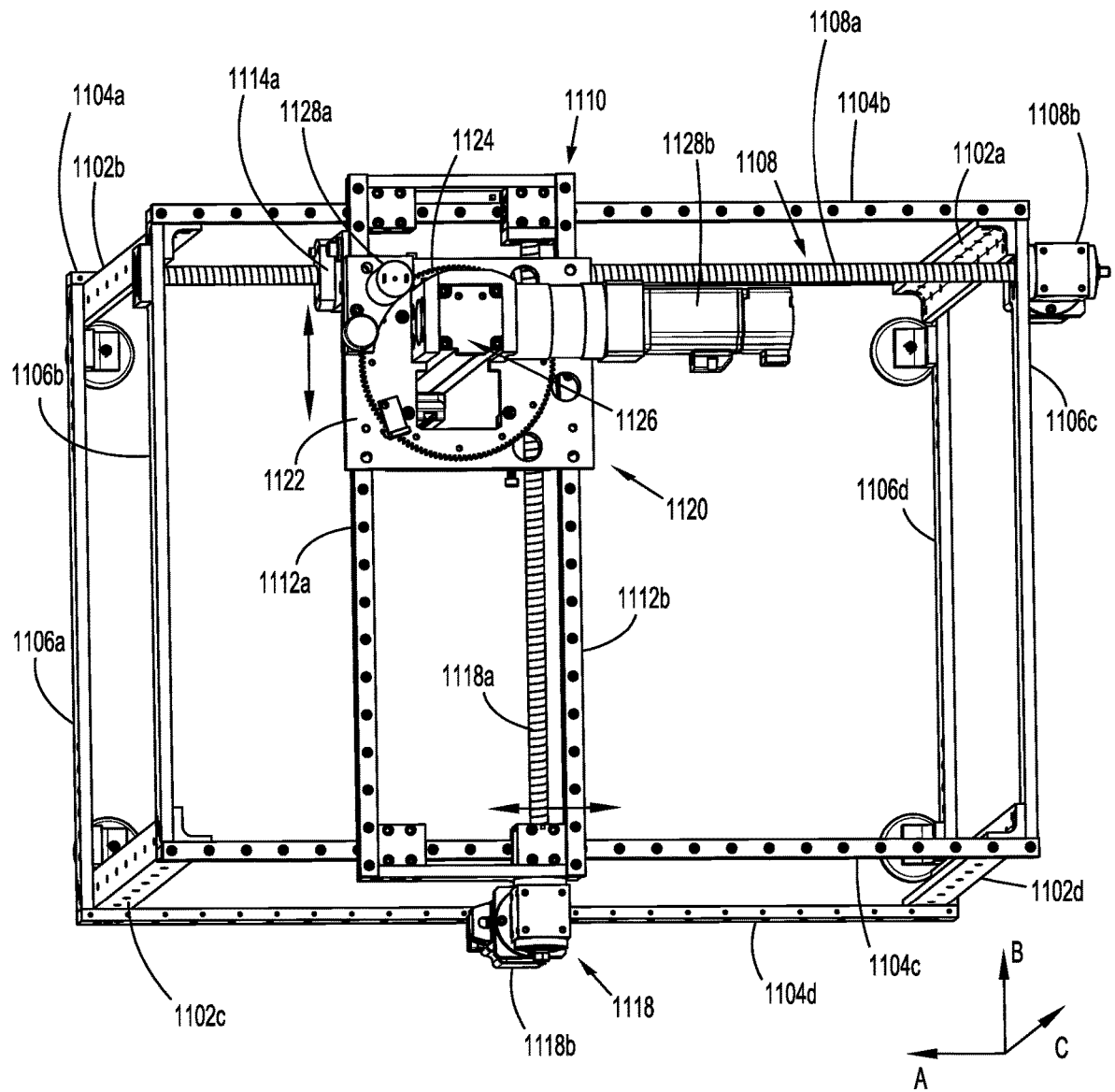
FIG. 16 is a second, perspective view of the preparation system of FIG. 14, with components removed therefrom.

Turning now to FIGS. 14-16, preparation system 1000 includes a frame 1100 having a substantially cubicle configuration made up of a plurality for studs or posts 1102a-1102d each extending along a respective "C" axis, a plurality of first stringers or rails 1104a-1104d each extending along a respective "A" axis and interconnecting selected posts 1102a-1102d, and a plurality of second stringers or rails 1106a-1106d each extending along a respective "B" axis and interconnecting selected posts 1102a-1102d. Frame 1100 provides the structure to support motion of various components of preparation system 1000 in a Cartesian horizontal plane. Frame 1100 is configured to promote clear air flow from top to bottom while frame 1100 is disposed within a hood (not shown).

Preparation system 1000 includes a gantry assembly 1110 slidably supported on upper, first stringer or rails 1104b, 1104c of frame 1100, for translation along the "A" axis. Gantry assembly 1110 may be supported atop upper, first stringer or rails 1104b, 1104c by bearings, low-friction slides or the like. It is contemplated that any structure or device capable of providing sliding support between gantry assembly 1110 and upper, first stringer or rails 1104b, 1104c may be employed.

Frame 1100 includes a gantry translation assembly 1108 configured to cause gantry assembly 1110 to translated along upper, first stringer or rails 1104b, 1104c of frame 1100, in the direction of the "A" axis. Gantry translation assembly 1108 includes a threaded gantry rod (e.g., screw) 1108a rotatably supported between upper, second stringer or rails 1106b, 1106c of frame 1100, and extending along a respective "A" axis. Gantry translation assembly 1108 further includes a motor 1108b connected to threaded gantry rod 1108a in such a manner that motor 1108b causes threaded gantry rod 1108a to rotate in a first and a second direction (e.g., clockwise and counter-clockwise).

Gantry assembly 1110 includes a pair of rails 1112a, 1112b each extending along a respective "B" axis. Gantry assembly 1110 further includes at least one threaded nut structure 1114a which threadably receives threaded gantry rod 1108a of gantry translation assembly 1108 therethrough (e.g., a ballscrew construction or configuration). In operation, as motor 1108b of gantry translation assembly 1108 rotates threaded gantry rod 1108a, gantry assembly 1110 is caused to translate along upper, first stringer or rails 1104b, 1104c of frame 1100, in the direction of the "A" axis.

Preparation system 1000 includes a turntable assembly 1120 slidably supported on rails 1112a, 1112b of gantry assembly 1110, for translation along the "B" axis. Turntable assembly 1120 may be supported atop 1112a, 1112b of gantry assembly 1110 by bearings, low-friction slides or the like. It is contemplated that any structure or device capable of providing sliding support between turntable assembly 1120 and 1112a, 1112b may be employed.

Gantry assembly 1110 includes a turntable translation assembly 1118 configured to cause turntable assembly 1120 to translated along rails 1112a, 1112b of gantry assembly 1110, in the direction of the "B" axis. Turntable translation assembly 1118 includes a threaded turntable rod (e.g., screw) 1118a rotatably supported on rail 1112b of gantry assembly 1110, and extending along a respective "B" axis. Turntable translation assembly 1118 further includes a motor 1118b connected to threaded turntable rod 1118a in such a manner that motor 1118b causes threaded turntable rod 1118a to rotate in a first and a second direction (e.g., clockwise and counter-clockwise).

Turntable assembly 1120 includes a platform 1122 supported on rails 1112a, 1112b of gantry assembly 1110. Turntable assembly 1120 further includes at least one threaded nut structure (not shown) which threadably receives threaded turntable rod 1118a of turntable translation assembly 1118 therethrough (e.g., a ballscrew construction or configuration). In operation, as motor 1118b of turntable translation assembly 1118 rotates threaded turntable rod 1118a, turntable assembly 1120 is caused to translate along rails 1112a, 1112b of gantry assembly 1110, in the direction of the "B" axis.

Turntable assembly 1120 includes a spur gear 1124 rotatably supported on platform 1122, wherein an axis of rotation of spur gear 1124 extending in a respective "C" axis. Turntable assembly 1120 further includes a rail column 1126 depending from, and non-rotatably connected to, spur gear 1124, wherein rail column 1126 extending along a respective "C" axis. Turntable assembly 1120 also includes a first motor 1128a in driving engagement with spur gear 1124 in such a manner that first motor 1128a causes spur gear 1124 to rotate in a first and a second direction (e.g., clockwise and counter-clockwise). Being that rail column 1126 is non-rotatably connected to spur gear 1124, as first motor 1128a rotates spur gear 1124, rail column 1126 is also concomitantly rotated.

Specifically, rail column 1126 is provided with rotation by way of a DC brushed gearmotor 1128a. Reversal of first motor 1128a is effected, for example, by computer control of relays acting on opposite polarity power supplies with one providing +12 VDC, and the other providing −12 VDC. Further, it is contemplated that reed switches are provided to assure complete rotation (or a completion of the needed or desired rotation) before subsequent program execution. The rotation of rail column 1126 is afforded by way of a pinion gear (not shown) mounted on first motor 1128a which drives spur or bull gear 1124. As mentioned above, rail column 1126 depends through the center of spur gear 1124 and is supported by a four point contact thin wall section bearing.

Preparation system 1000 includes a carriage 1130 translatably supported on rail column 1126 of turntable assembly 1120. Translation of carriage 1130 along rail column 1126 is achieved by a second motor 1128b of turntable assembly 1120 driving a threaded rod (not shown) extending through rail column 1126 and threadably engaging a threaded nut structure (not shown) fixed to carriage 1130 (e.g., a ballscrew construction or configuration).

Preparation system 1000 includes a gripper (G) secured to carriage 1130. The gripper (G) is responsible for grasping a compounding component, retained in the component holder (CH), removing the compounding component from a station of preparation system 1000 or from the component holder (CH), and then placing compounding component in another station of preparation system 1000. The gripper (G) is also responsible for returning a compounding component from a station to the component holder (CH). The gripper (G) is further responsible for effecting the assembly and disassembly of the sub-assemblies, specifically a vial (V) and vial adapter 13 sub-assembly (e.g., vial assembly), and a syringe "I" and syringe adapter 11 sub-assembly (e.g., syringe assembly).

Figure 17:
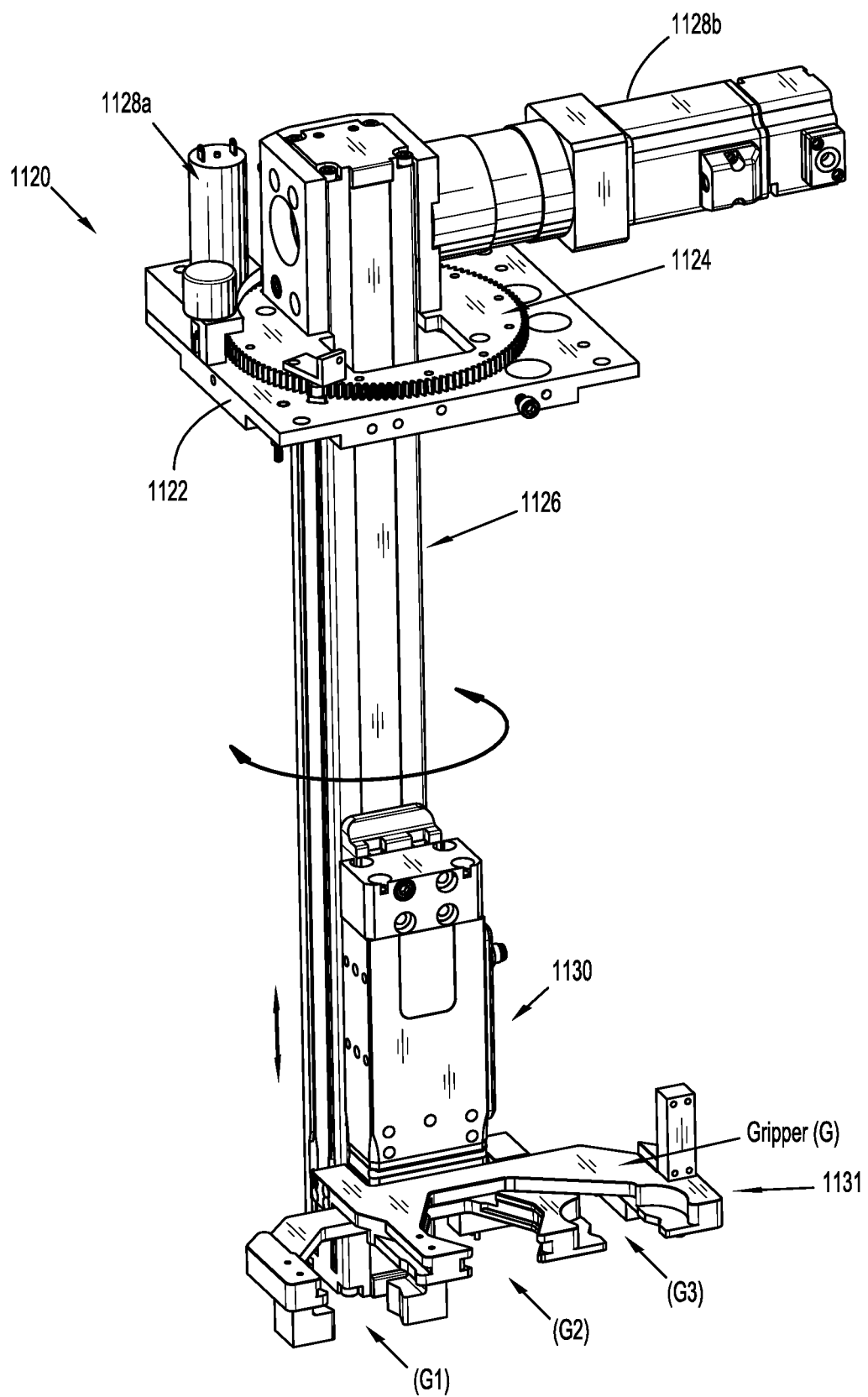
FIG. 17 is a perspective view of a turntable assembly of the preparation system of FIG. 14.
Figure 18:
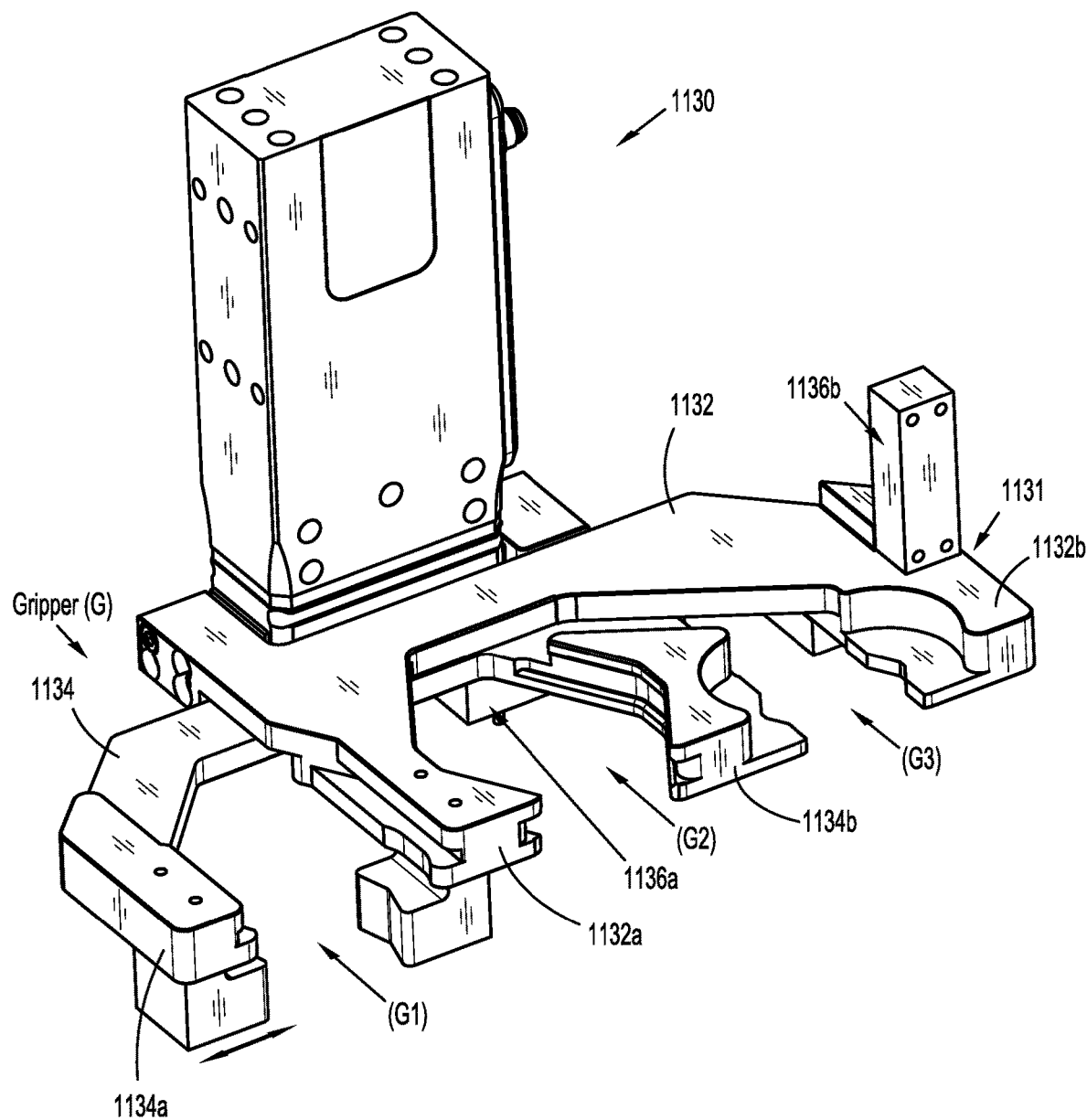
FIG. 18 is a perspective view of a carriage and a gripper of the preparation system of FIG. 14.

With reference to FIGS. 17 and 18, the gripper (G) includes two jaws that can adapt to four components, by way of hermaphroditic jaws 1131 (including a first pair of fixed, opposed jaws 1132, and a second pair of translatable, opposed jaws 1134, wherein one jaw of the first pair of jaws 1132 is interposed between the second pair of jaws 1134, and wherein a second jaw of the second pair of jaws 1134 is interposed between the first pair of jaws 1132) thereof. The gripper (G) features jaws 1131 that are coordinated by way of two gear racks and a pinion so that the jaws 1131 always open and close on a fixed center plane.

As illustrated in FIG. 18, the gripper (G) functions by translating the first pair of jaws 1132 and the second pair of jaws 1134 relative to one another to grip a component (e.g., a syringe "I", a vial "V", a syringe adapter 11, a vial adapter 13, etc.) in one of a first gripping position (G1), a second gripping position (G2) and a third gripping position (G3). The first gripping position (G1) may be located between a first jaw 1132a of the first pair of jaws 1132 and a first jaw 1134a of the second pair of jaws 1134; the second gripping position (G2) may be located between the first jaw 1132a of the first pair of jaws 1132 and a second jaw 1134b of the second pair of jaws 1134; and the third gripping position (G3) may be located between a second jaw 1132b of the first pair of jaws 1132 and the second jaw 1134b of the second pair of jaws 1134.

By way of example only, the first gripping position (G1) of the gripper (G) may be used to grip a syringe "I", the second gripping position (G2) of the gripper (G) may be used to grip a vial adapter 13, and the third gripping position (G3) of the gripper (G) may be used to grip a syringe adapter 11.

The gripper (G) is configured as hermaphroditic, which configuration allows for multiple uses of each of the gripper positions, for instance the gripping position (G1) can be used to grasp the head or upper extent of syringe "I" as well as the lower extent of syringe "I", thus affording more flexibility. The jaws 1131 of the gripper (G) may be actuated by a motor or the like, e.g., Destaco Robohand manipulator. The jaws 1131 of the gripper (G) are further configured to provide measurement and error trapping. For example, a horizontal linear potentiometer 1136a provides for the diametral measurement of components, such as syringes "I" and vials "V" to ensure the correct diameter is grasped, while a vertical linear potentiometer 1136b is provided for the locating of a raises feature or rib projecting from the vial adapter 13.

In use, carriage 1130, and in turn, the gripper (G), is translatable along the length of rail column 1126 upon an actuation of second motor 1128b; and carriage 1130 and the gripper (G) are rotatable about the longitudinal axis of rail column 1126 upon an actuation of first motor 1128a.

Figure 19:
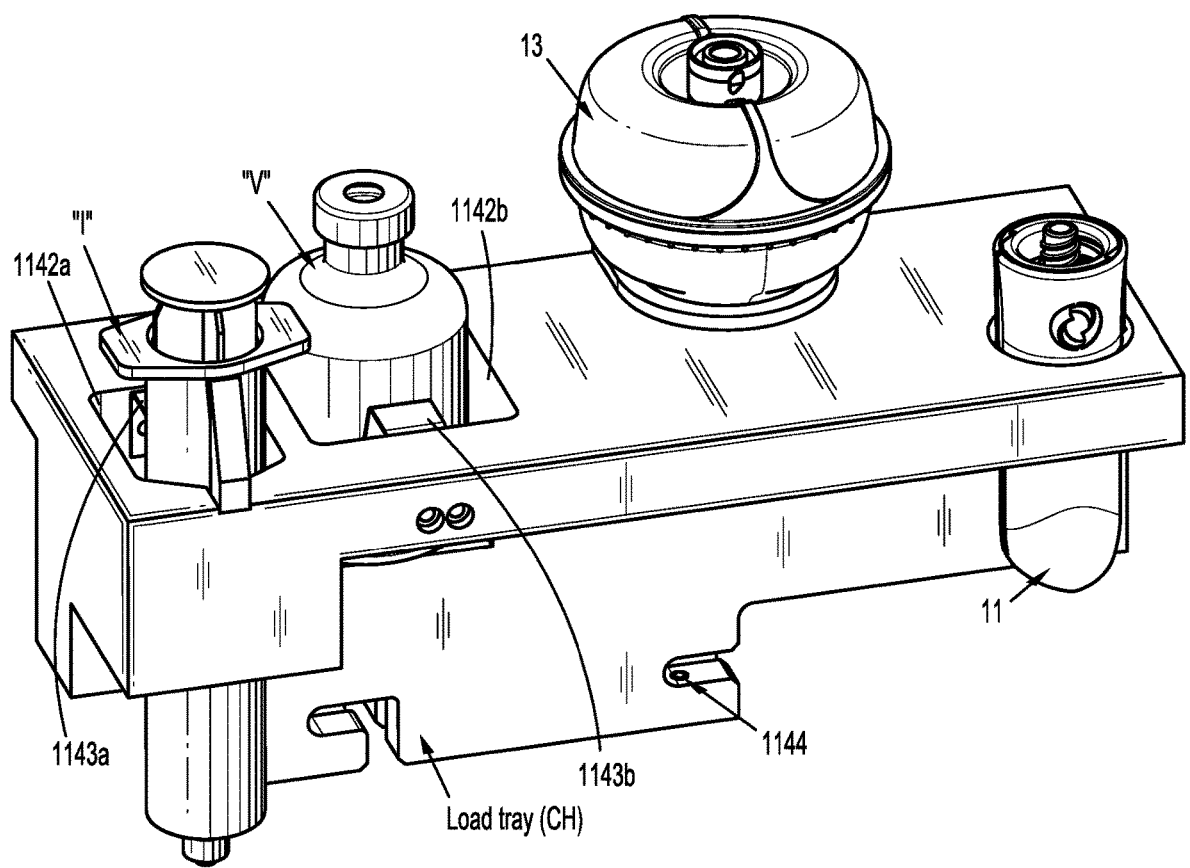
FIG. 19 is a perspective view of a load tray of the preparation system of FIG. 14.

Turning now to FIGS. 14 and 19, preparation system 1000 includes a component holder or load tray (CH) secured to frame 1100 which is configured to retain moveable components utilized in a compounding cycle of preparation system 1000. The moveable components include, as illustrated in FIGS. 1 and 14, a vial "V", a vial adapter 13, a syringe "I" and a syringe adapter 11. The vial adapter 13 may be sized to accommodate a 20 mm neck of a vial "V". The vial adapter 13 is staged or retained in a recess (not shown) in the load tray (CH), such that a protective cover of vial adapter 13 resides beneath a top wall of the load tray (CH) and is configured to strip of remove the cover of the vial adapter 13 upon vertical translation of vial adapter 13.

Load tray (CH) includes recesses formed therein for selectively retaining the moveable components. For example, load tray (CH) may include a recess 1142a configured to retain syringe "I", and a recess 1142b configured to retain a vial "V". Recesses 1142a, 1142b of the load tray (CH) may be configured to have a V-shaped profile and be provided with a respective leaf spring 1143a, 1143b in order to accommodate different diameters of movable components therein.

The load tray (CH) may be configured for support or staging on lower, first stringer or rail 1104a of frame 1100 by way of four posts or the like, and may include a spring loaded plunger and detent feature 1144 for repeated connection disconnection to/from lower, first stringer or rail 1104a.

Figure 20A:
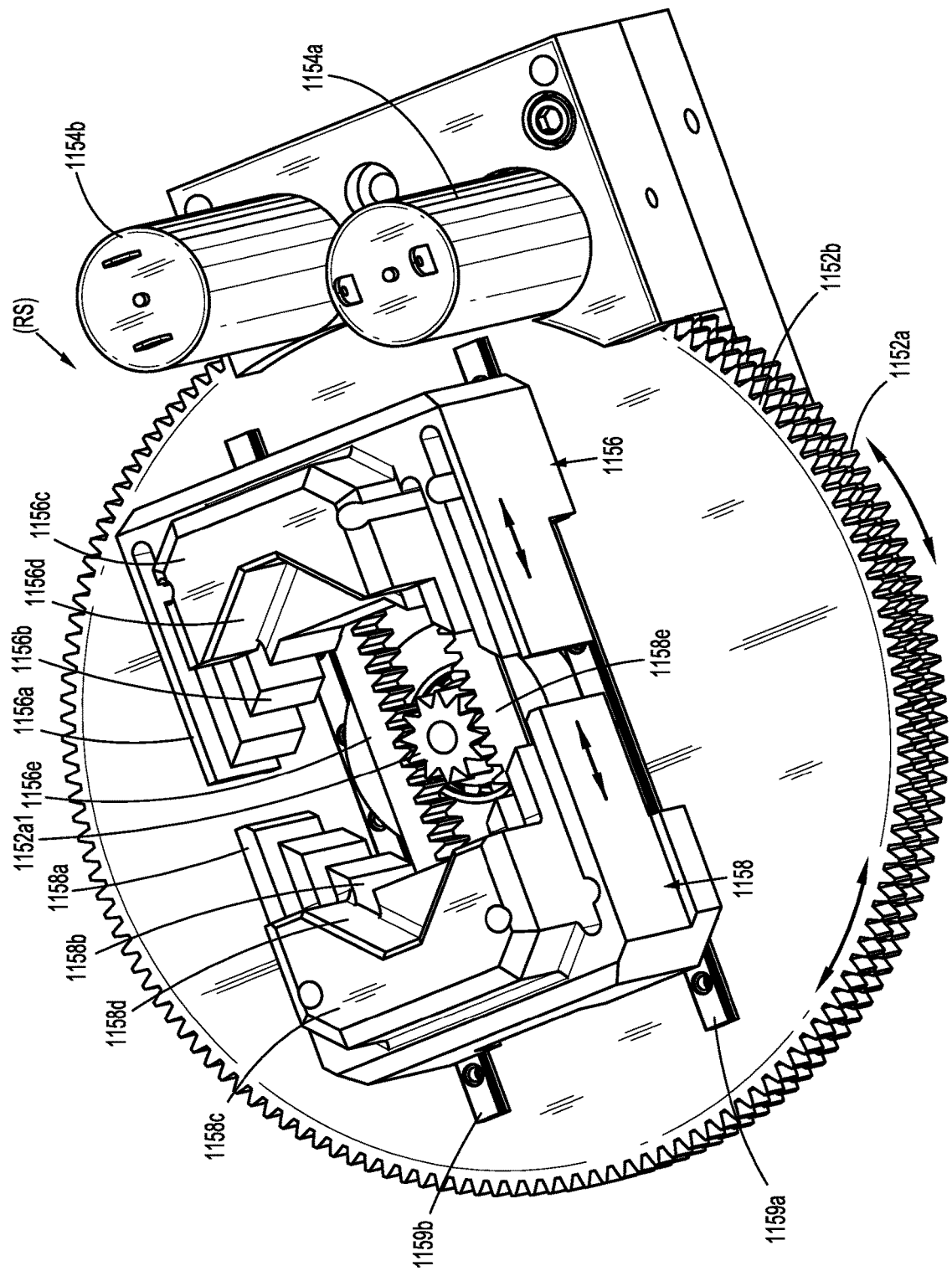
FIG. 20A is a perspective view of a rotation station of the preparation system of FIG. 14.
Figure 20B:
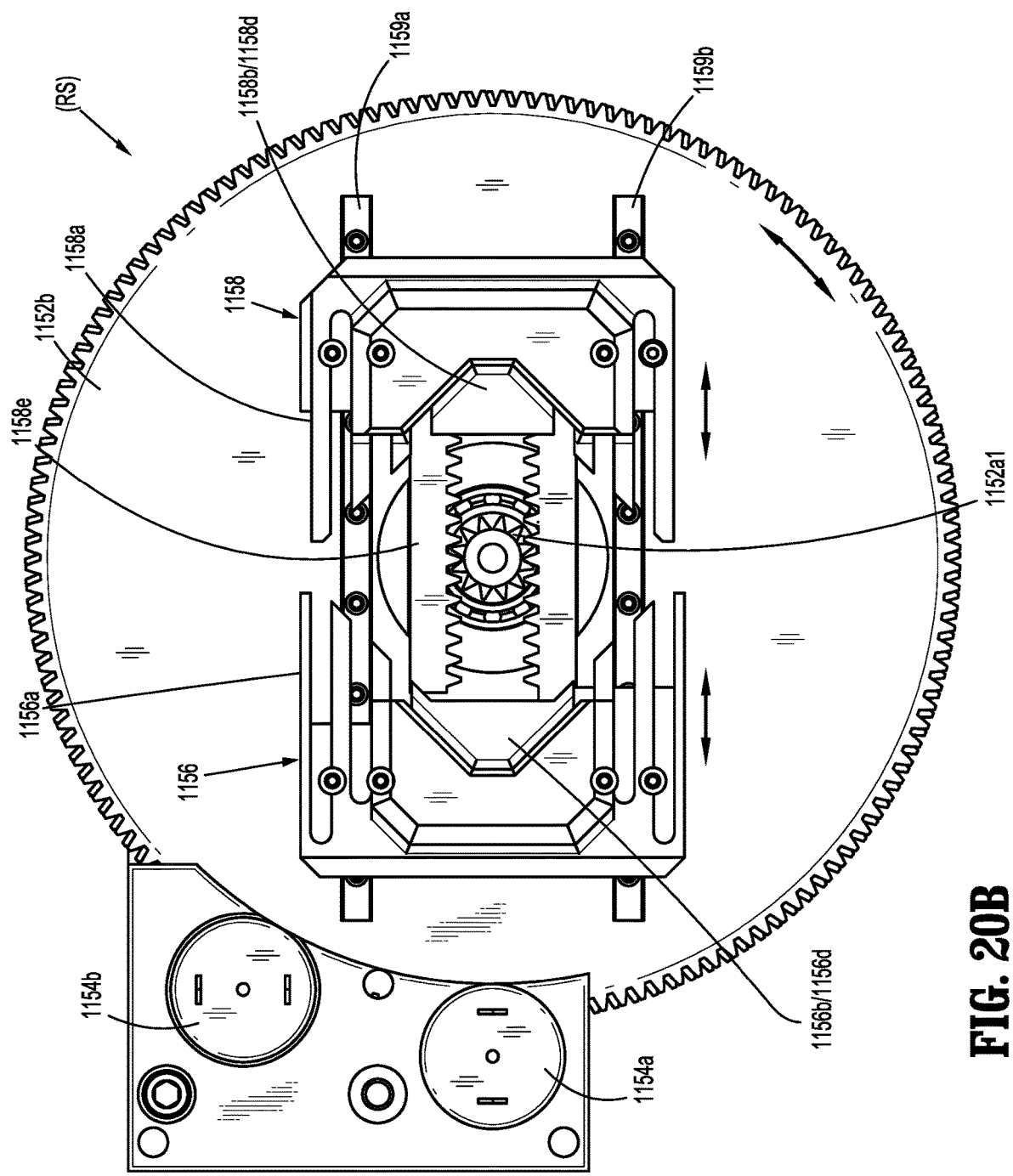
FIG. 20B is a top, plan view of the rotation station of FIG. 20A.
Figure 21A:
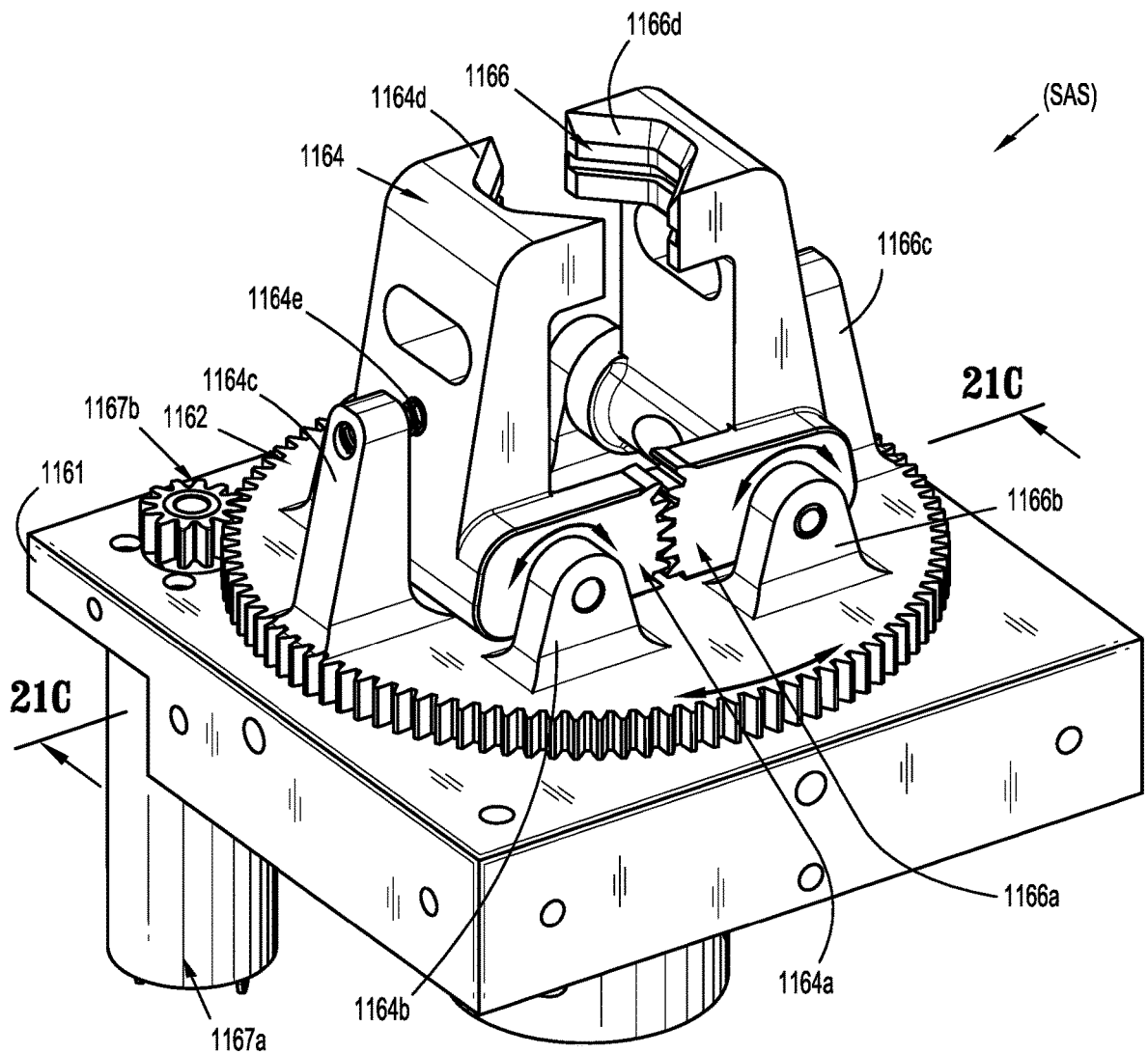
FIG. 21A is a perspective view of a syringe adapter station of the preparation system of FIG. 14.
Figure 21B:
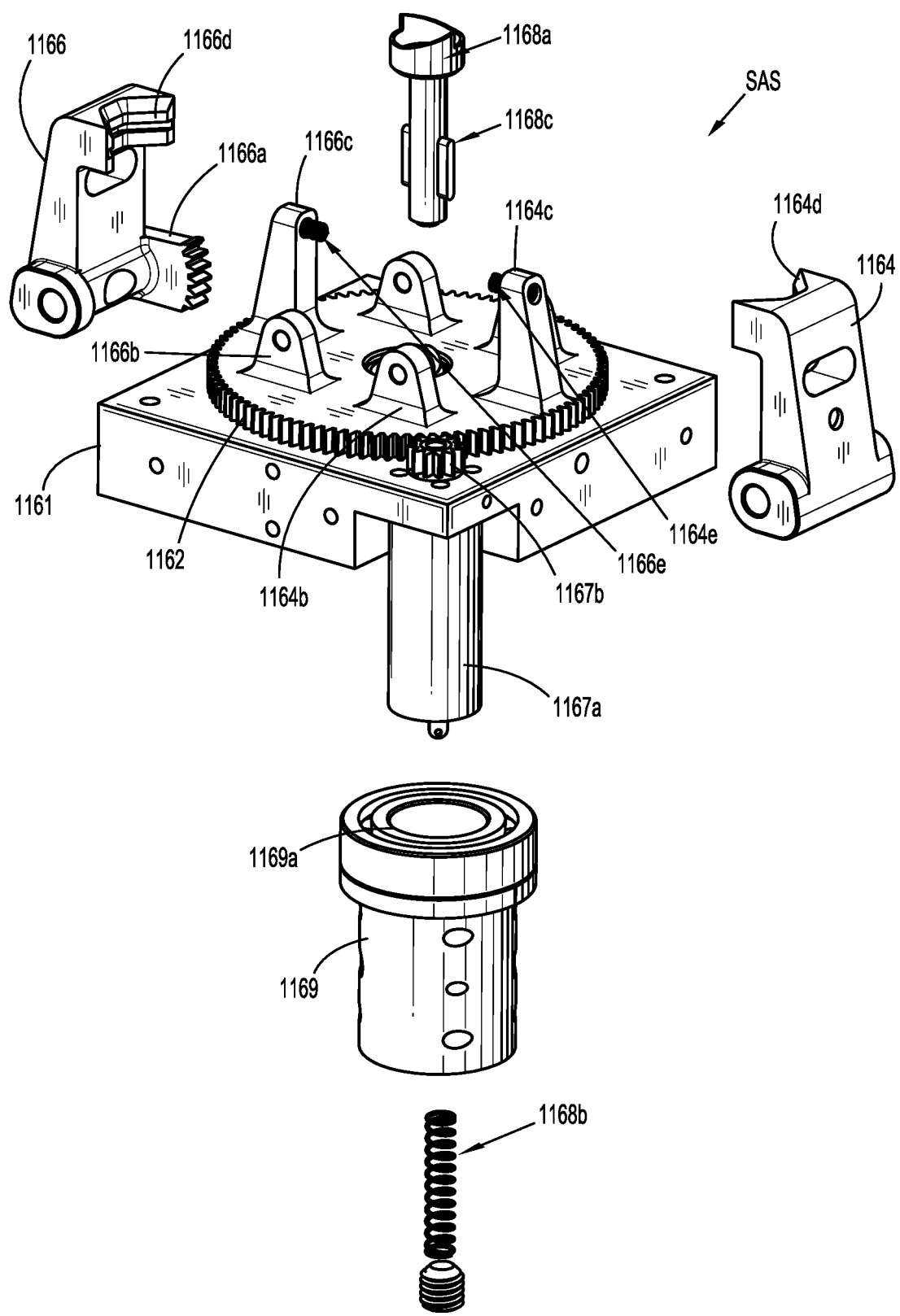
FIG. 21B is a further perspective view, with parts separated, of the syringe adapter station of FIG. 21A.
Figure 21C:
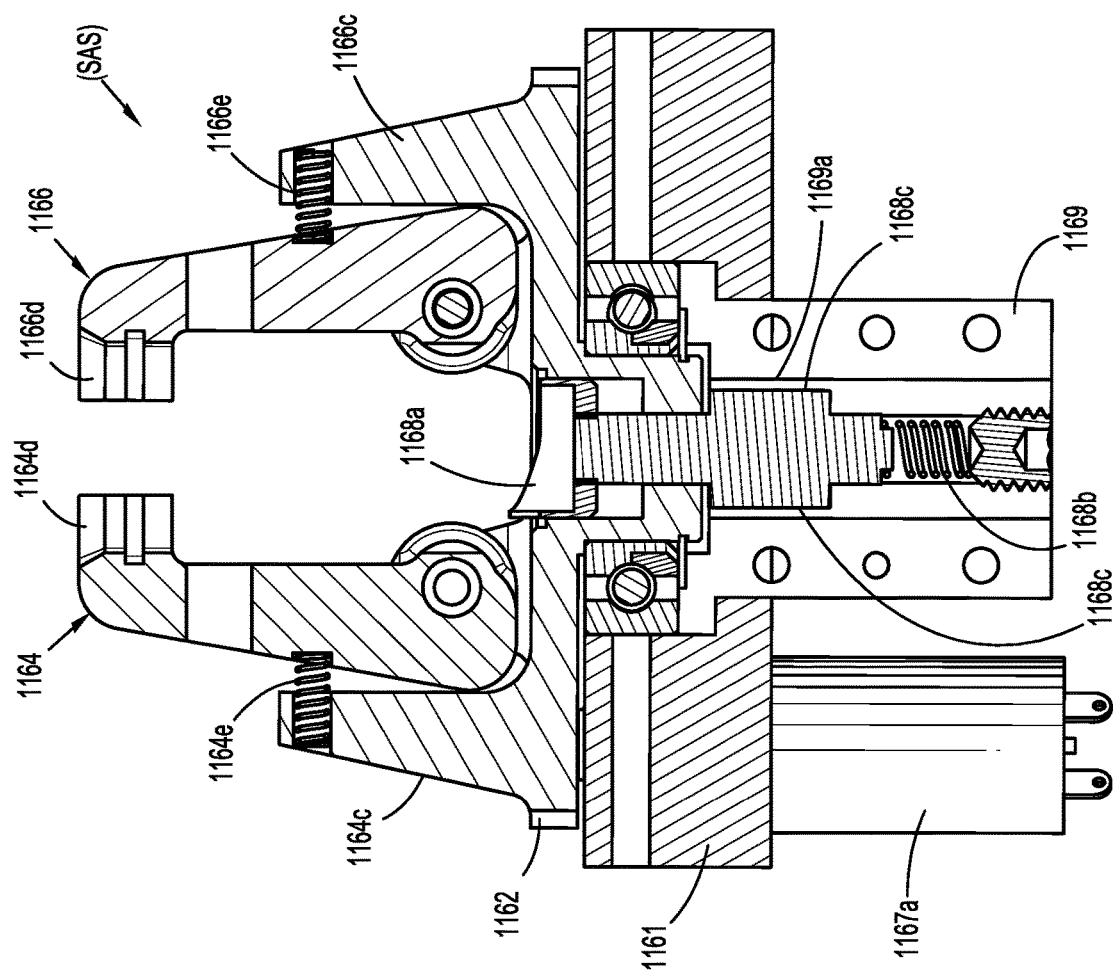
FIG. 21C is a cross-sectional view of the syringe adapter station of FIGS. 21A-21B as taken through 21C-21C of FIG. 21A.

Turning now to FIGS. 14 and 20A-20B, preparation system 1000 includes a rotation station (RS) secured to frame 1100 (e.g., to a floor of frame 1100). Rotation station (RS) provides a clamping function for the assembly and disassembly of selected moveable components, and provides a rotation function to phase vial adapter 13 for connection with syringe adapter 11.

Rotation station (RS) includes two bull or spur gears 1152a, 1152b are mounted with a small vertical axial clearance therebetween. The lower spur gear 1152a is driven by a first motor 1154a, e.g., a bidirectional DC gearmotor, and serves to drive a pinion 1152a1 and a pair of racks 1156e, 1158e for the opening and closing of a pair of jaws 1156, 1158 of rotation station (RS). The pair of jaws 1156, 1158 are translatably supported on upper spur gear 1152b by way of rails 1159a, 1159b. Bi-directionality of first motor 1154a is afforded by switching between two opposite polarity power supplies.

In operation, a first actuation of first motor 1154a causes lower spur gear 1152a to rotate in a first direction, and in turn, causes concomitant rotation of pinion 1152a1 in a first direction. As pinion 1152a1 is rotated in the first direction, pinion 1152a1 acts on the pair of racks 1156e, 1158e of the pair of jaws 1156, 1158 to axially slide the pair of racks 1156e, 1158e in a first direction (opposite to one another). As the pair of racks 1156e, 1158e slide in the first direction, the pair of jaws 1156, 1158 are approximated towards one another (e.g., closing the pair of jaws). It follows that a second actuation of first motor 1154a (opposite the first actuation) causes lower spur gear 1152a to rotate in a second direction (opposite the first direction), and in turn, causes concomitant rotation of pinion 1152a1 in a second direction. As pinion 1152a1 is rotated in the second direction, pinion 1152a1 acts on the pair of racks 1156e, 1158e of the pair of jaws 1156, 1158 to axially slide the pair of racks 1156e, 1158e in a second direction (opposite to one another). As the pair of racks 1156e, 1158e slide in the second direction, the pair of jaws 1156, 1158 separate from one another (e.g., opening the pair of jaws).

The upper spur gear 1152b is responsible for the rotation of the entire rotation station (RS). The upper spur gear 1152b is driven by a second motor 1154b, e.g., a DC gearmotor, having a higher ratio than that for the first motor 1154a. Thus the pair of jaws 1156, 1158 can open and close without back-driving the rotational gear or upper spur gear 1152b.

It is contemplated that the jaw or first motor 1154a operates at a higher speed than the rotation or second motor 1154b, such that, during rotation of rotation station (RS), a torque is maintained on a jaw transmission, and a magnetic field of the jaw or first motor 1154a simply slips along at the rate of the second or rotation motor 1154b.

The pair of jaws 1156, 1158 are configured with passing fingers/walls that define an upper vial position and a lower vial position, increasing the range of vial diameter and length that can be accommodated. Specifically, each jaw 1156, 1158 includes a plurality of spaced apart and parallel walls 1156a, 1158a, respectively, wherein the walls 1156a of first jaw 1156 are in registration or aligned with the gaps defined between walls 1158a of second jaw 1158. In this manner, as the pair of jaws 1156, 1158 are approximated towards one another, the respective walls 1156a, 1158a intermesh or nest with one another. The walls 1156a of first jaw 1156 define a substantially V-shaped or tapering and converging profile or recess 1156b, and the walls 1158a of second jaw 1158 define a substantially V-shaped or tapering and converging profile or recess 1158b, wherein the recesses 1156b, 1158b are in opposed relation to one another, thus defining the lower vial position.

Each jaw 1156, 1158 supports a respective upper grip block 1156c, 1158c. Each grip block 1156c, 1158c is located near a rear end of respective walls 1156b, 1158b of the pair of jaws 1156, 1158. Each grip block 1156c, 1158c defines a respective substantially V-shaped or tapering and converging profile or recess 1156d, 1158d, wherein the recesses 1156d, 1158d are in opposed relation to one another, and wherein the recesses 1156d, 1158d are in registration with the recesses 1156b, 1158b defined by walls 1156a, 1158a, thus defining the upper vial position.

Turning now to FIGS. 14, and 21A-21C, preparation system 1000 includes a syringe adapter station (SAS) secured to frame 1100. Syringe adapter station (SAS) includes a platform 1161 rotatably supporting a bull or spur gear 1162 thereon. Syringe adapter station (SAS) further includes a pair of spring loaded vertical jaws 1164, 1166 that are synchronized by respective gearing 1164a, 1166a projecting therefrom to coordinate the gripping of a syringe adapter 11. The pair of jaws 1164, 1166 are pivotally supported on spur gear 1162 by respective supports 1164b, 1166b projecting from spur gear 1162. The pair of jaws 1164, 1166 are disposed between respective uprights 1164c, 1166c projecting from spur gear 1162. Each jaw 1164, 1166 includes a respectively, substantially V-shaped notch or recess 1164d, 1166d formed in an end thereof and configured and dimensioned to at least partially surround a syringe adapter 11. A pair of respective biasing members 1164e, 1166e is disposed between respective jaws 1164, 1166 and respective uprights 1164c, 1166c.

Syringe adapter station (SAS) includes a saw-tooth shaped cup 1168a slidably supported in a floor of platform 1161, and located between the pair of jaws 1164, 1166. A biasing member 1168b is provided to urge saw-tooth shaped cup 1168a towards the pair of jaws 1164, 1166 and out of platform 1161. Saw-tooth shaped cup 1168a includes at least one tab 1168c projecting radially from a surface thereof and which slidably resides in a channel or groove 1169a of a housing or shroud 1169, wherein the housing 1169 is secured to spur gear 1162.

In operation, for an assembly of a syringe adapter 11 and a syringe "I" to one another, a syringe adapter 11 is first retained between the pair of jaws 1164, 1166 of syringe adapter station (SAS) such that luer connector 69 (FIGS. 1-4) of syringe adapter 11 projects away from platform 1161. Syringe adapter 11 is seated in saw-tooth shaped cup 1168a in such a manner that syringe adapter 11 may only rotate in a single direction. Next, a syringe "I", is picked up from load tray (CH) by gripper (G) and approximated toward syringe adapter station (SAS) by gantry assembly 1110 until a luer connector of the syringe "I" is axially aligned with luer connector 69 of syringe adapter 11, and advanced toward syringe adapter 11 until syringe adapter 11 is pressed slighted against saw-tooth shaped cup 1168a.

A motor 1167a (e.g., a bi-directional gearmotor) then rotates spur gear 1161 (in a first direction), by way of a pinion gear 1167b, to rotate syringe adapter 11 relative to syringe "I". With saw-tooth shaped cup 1168a preventing syringe adapter 11 from rotating relative to spur gear 1162, as syringe adapter 11 is rotated relative to syringe "I", a connection between the luer connectors thereof is achieved, thereby assembling syringe adapter 11 and syringe "I". During assembly, saw-tooth shaped cup 1168a rides up and down on surface features provide on the end of syringe adapter 11.

Once syringe adapter 11 and syringe "I" are assembled, spur gear 1162 is rotated in an opposite direction by rotating spur gear 1162. As the assembled syringe adapter 11 and syringe "I" are rotated in the opposite direction, with gripper (G) disengaged from syringe "I", the saw-tooth shaped cup 1168a engages features provided in an end of the syringe adapter 11 to thereby provide orientation to the assembled syringe adapter 11 and syringe "I" for later assembly of the syringe adapter 11 to a vial adapter 13, I.V. adapter 15, or I.V. bad adapter 17.

Figure 22:
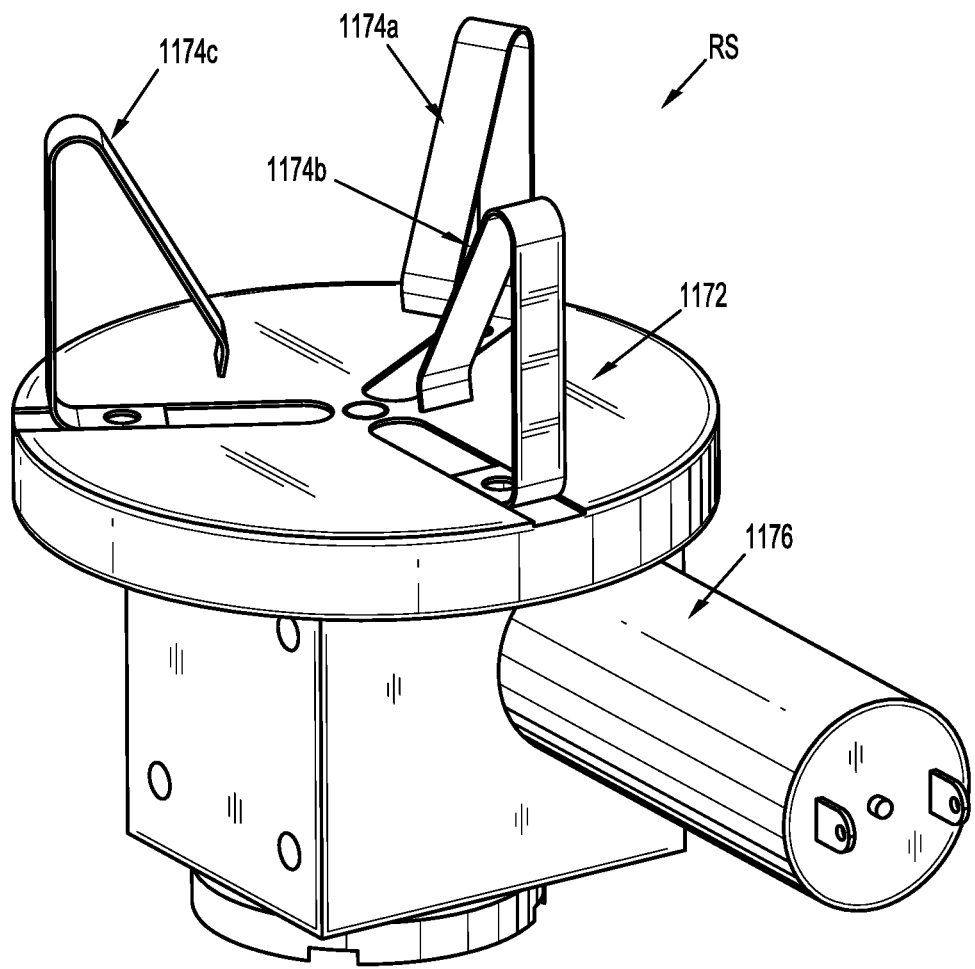
FIG. 22 is a perspective view of a reconstitution station of the preparation system of FIG. 14.

Turning now to FIGS. 14 and 22, preparation system 1000 includes a reconstitution station (W/RS) secured to frame 1100. Reconstitution station (W/RS) provides agitation for the dissolution of a lyophilized drug. In operation, reconstitution station (W/RS) may be activated while other compounding is underway in preparation system 1000.

Reconstitution station (W/RS) includes a turntable 1172 supporting at least three leaf springs 1174a-1174c on a first surface thereof. Leaf springs 1174a-1174c are radially arranges around a central axis of rotation of turntable 1172. Each leaf spring 1174a-1174c includes a leg portion secured to and extending away from turntable 1172, and an arm portion extending from a free end of a respective leg and toward the central axis of rotation of turntable 1172. Leaf springs 1174a-1174c function to stabilize and selectively retain vials of various diameters therebetween.

Reconstitution station (W/RS) includes a motor 1176 that is in operative engagement with turntable 1172 to provide agitation to turntable 1172, and in turn a vial "V" supported thereon, upon an on-off excitation of motor 1176 via a programmable relay to drive the turntable 1172 through, for example, a gearing arrangement (e.g. a worm gear) or the like.

Figure 23:
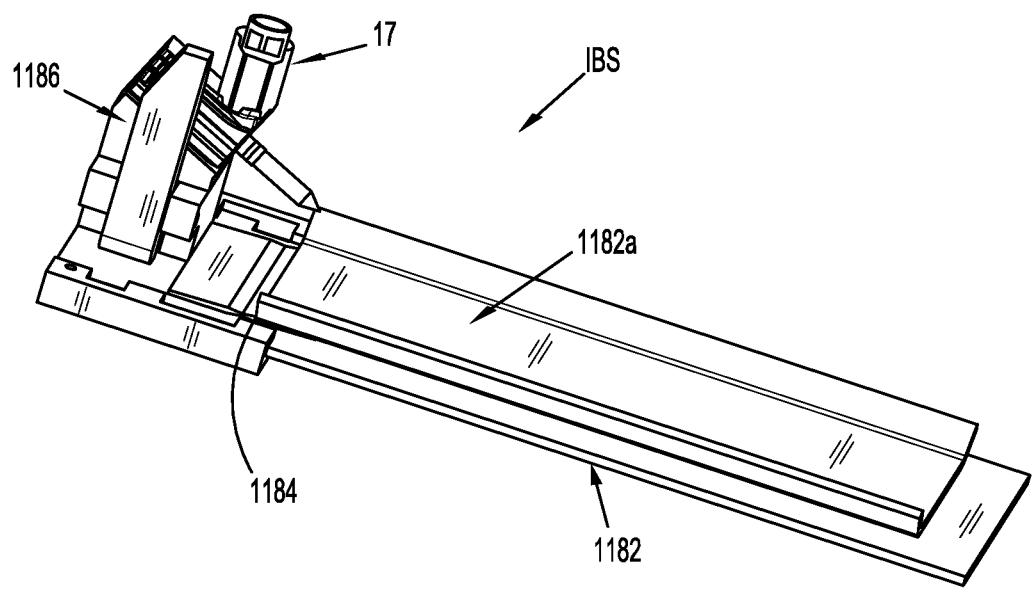
FIG. 23 is a perspective view of an infusion bag station of the preparation system of FIG. 14.

Turning now to FIGS. 14 and 23, preparation system 1000 includes an infusion bag station (IBS) secured to frame 1100. Infusion bag station (IBS) is positioned in frame 1100 so that tubes of an infusion bag project away from the moving parts of preparation system 1000.

Infusion bag station (IBS) includes a tray 1182 that snaps into a detent 1184 for positioning thereof. Infusion bag station (IBS) further includes a bag adapter block 1186 having a shape and/or configuration that is complimentary to and outer profile of I.V. bag adapter 17. The I.V. bag adapter 17 and an I.V. bag (not shown) can be loaded and unloaded into the infusion bag station (IBS) with a single hand, and is/are held in place by a spring loaded arm 1188 of infusion bag station (IBS). Tray 1182 includes a sub-tray 1182a, so that, if so desired, sub-tray 1182a can be angled from the horizontal.

Figure 24:
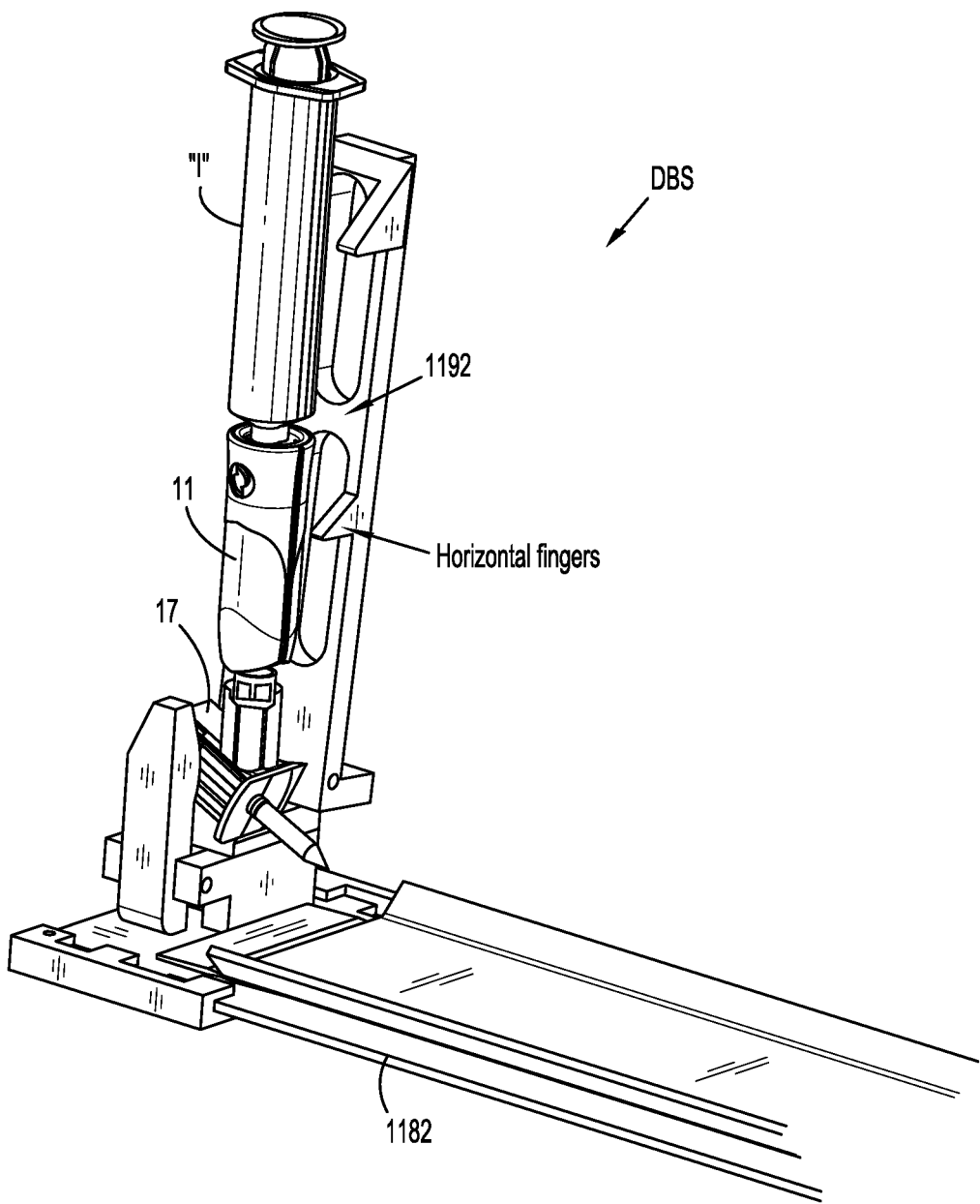
FIG. 24 is a perspective view of a diluent bag station of the preparation system of FIG. 14.

Turning now to FIGS. 14 and 24, preparation system 1000 includes a diluent bag station (DBS) secured to frame 1100. Diluent bag station (DBS) is positioned in frame 1100 so that tubes of a diluent bag project away from the moving parts of preparation system 1000.

Diluent bag station (DBS) stages a diluent bag (not shown) for extraction of liquid therefrom for the reconstitution of lyophilized drug. Diluent bag station (DBS) is configured similarly to infusion bag station (IBS), but is further provided with a vertical arm 1192 extending from a tray 1182 thereof. Vertical arm 1192 of diluent bag station (DBS) is configured to provide retention of a syringe adapter 11 while diluent (contained in diluent bag) is drawn, via syringe "I", by way of a pair of horizontal fingers 1192a projecting from vertical arm 1192. Specifically, with an I.V. bag adapter 17 fluidly connected to a diluent bag (not shown) and to a syringe adapter 11, and with a syringe "I" (having its plunger disposed in an advanced position) fluidly connected to the same syringe adapter 11, as the plunger is withdrawn, fluid or diluent is drawn from diluent bag, through I.V. bag adapter 17 and syringe adapter 11, and into syringe "I".

Vertical arm 1192 of diluent bag station (DBS) may be spring loaded to engage the syringe "I", the syringe adapter 11, and the assembly thereof. Vertical arm 1192 is further provided with features to engage the jaws 1132, 1134 of gripper (G) to allow the loading and unloading of the syringe and syringe adapter assembly to/from diluent bag station (DBS).

Figure 25:
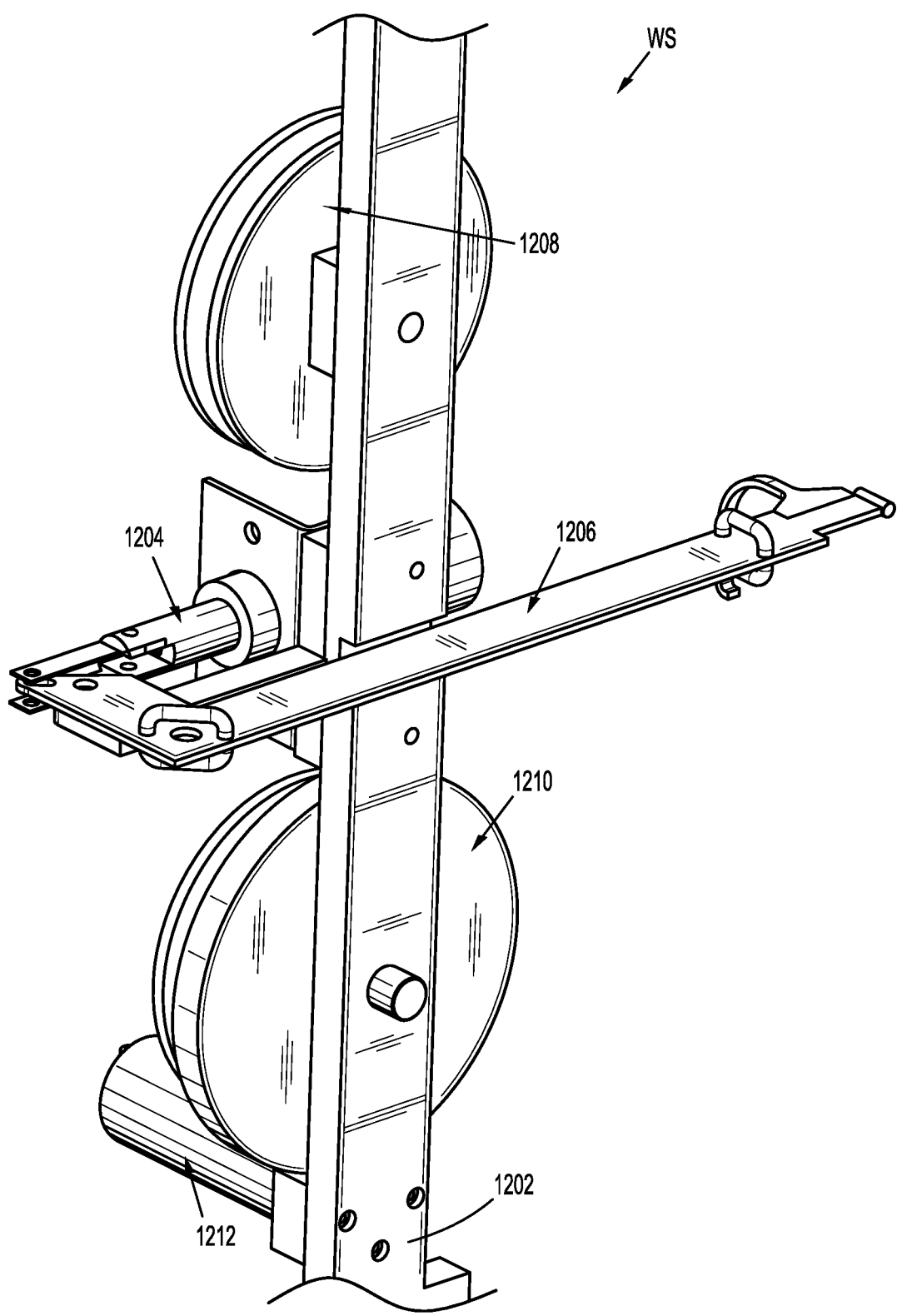
FIG. 25 is a perspective view of a wipe station of the preparation system of FIG. 14.

Turning now to FIGS. 14 and 25, preparation system 1000 includes a wipe station (WS) secured to frame 1100. Wipe station (WS) is configured to provide an alcohol wipe (not shown) to the glands or seals of the vial adapter 13 and the syringe adapter 11, prior to an assembly to one another. This procedure is consistent with aseptic parts handling and provides additional protection from infection and contamination.

Wipe station (WS) includes a base 1202, a solenoid/spring assembly 1204 supported on baser 1202, a swing arm 1206 supported on base 1202 and operatively connected to solenoid/spring assembly 1204, an alcohol pump and dispersal system (not shown), a tape feed reel 1208 rotatably supported on base 1202 adjacent a first side of solenoid/spring assembly 1204, and take up reel 1210 rotatably supported on base 1202 adjacent a second side of solenoid/spring assembly 1204.

Wipe station (WS) includes tape (not shown) extending from tape feed reel 1208, around a landing of swing arm 1206, and into take up reel 1210. Wipe station (WS) further includes a motor 1212 operatively connected to take up reel 1210 to cause rotation of take up reel 1210 and a drawing out of the tape from tape feed reel 1208.

In operation, with the tape moistened with alcohol, by the alcohol pump and dispersal system (not shown), in the area of the landing of swing arm 1206, a vial adapter 13 or a syringe adapter 11 is picked up from load tray (CH) by gripper (G) and approximated toward wipe station (WS) by gantry assembly 1110 such that the seal thereof is brought into close proximity to the landing of swing arm 1206. With the seal of the vial adapter 13 or the syringe adapter 11 in close proximity to the landing of swing arm 1206, the solenoid of solenoid/spring assembly 1204 is actuated to move swing arm 1206, and in turn the alcohol moistened tape into contact with the seal. Thereafter, take up reel 1210 is rotated to draw the alcohol moistened tape across the seal and disinfect the seal. The process is repeated for the other of the vial adapter 13 or syringe adapter 11.

Figure 26:
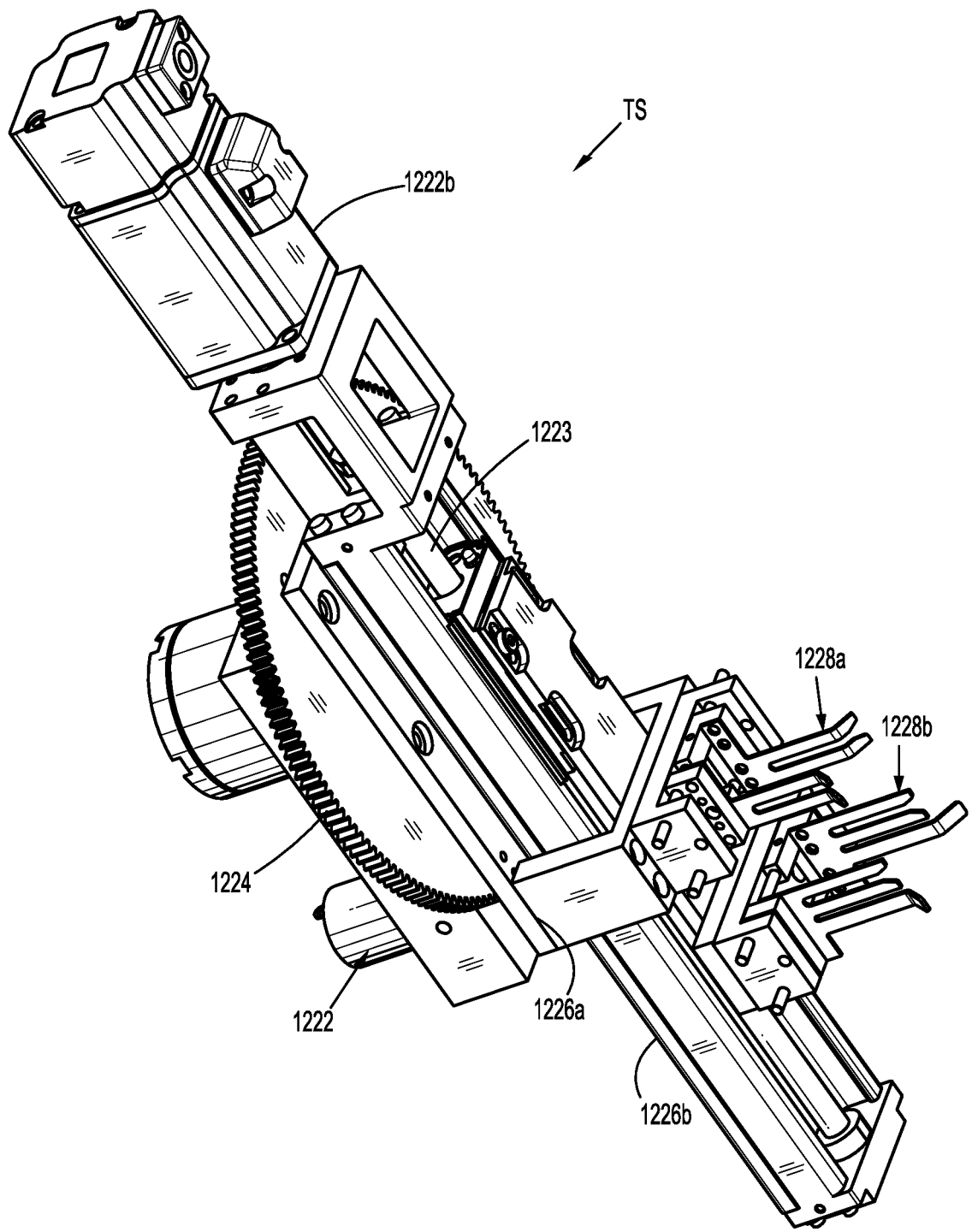
FIG. 26 is a perspective view of a transfer station of the preparation system of FIG. 14.

Turning now to FIGS. 14 and 26, preparation system 1000 includes a transfer station (TS) secured to frame 1100.

Transfer station (TS) provides for the transfer of fluids between the syringe "I" and the vial "V". Transfer station (TS) is configured for rotation about a horizontal axis by way of a first motor 1222*a*, e.g., a bidirectional gearmotor, operatively engaged with a bull or spur gear 1224 supported on a fixed frame 1226*a*. Transfer station (TS) further includes a pair of spring loaded jaws 1228*a*, 1228*b* for selective engagement with a plunger and plunger flanges of syringe "I". A first jaw 1228*a* is connected to fixed frame 1226*a*, and a second jaw 1228*b* is connected to a movable frame 1226*b*, wherein the movable frame 1226*b* is translatable connected to fixed frame 1226*a* to approximate and/or separate the pair of jaws 1228*a*, 1228*b*. The pair of jaws 1228*a*, 1228*b* may be mounted on linear bearings designed to move with minimal effort to accommodate syringes of differing volumes.

Transfer station (TS) may include a second motor 1222*b* that is in driving engagement with a threaded rod 1223 that is in threaded engagement with second jaw 1228*b*, wherein rotation of threaded rod 1223 by second motor 1222*b* results in translation of second jaw 1228*b* relative to first jaw 1228*a*.

For a more detailed discussion of the function and operation of transfer station (TS), reference may be made to U.S. Pat. No. 9,107,809, the entire content of which was previously incorporated herein by reference.

The operation of preparation system 1000, of the present disclosure, is highly flexible, with the ability to provide for the compounding of various drug, volumes, diluents, speeds, etc. Preparation system 1000 is capable of performing three basic routines for the preparation of a drug, namely, to push a dose from a syringe "I", to inject a dose into an infusion bag (not shown), and to reconstitute lyophilized drug.

In accordance with the present disclosure, a routine for pushing a dose includes the following steps:

1. Bring a vial "V" to rotation station (RS). Specifically, the pair of jaws 1132, 1134 of gripper (G) engage a neck of the vial "V", remove the vial "V" from the load tray (CH), and present the vial "V" to the rotation station (RS), where the pair of jaws 1156, 1158 of the rotation station (RS) close on a body of the vial "V". The pair of jaws 1132, 1134 of gripper (G) then release the vial "V" and return to a home position.
2. Assemble a vial adapter 13 to the vial "V". The pair of jaws 1132, 1134 of gripper (G) then grab a vial adapter 13 around an "equator" thereof, e.g., around a portion of vial adapter 13 between base 201 and cover 215 of the vial adapter 13, position the vial adapter 13 over the vial "V", and press the vial adapter 13 and the vial "V" together in a downwards motion (e.g., by approximating the vial adapter 13 and the vial "V") to form a vial assembly, and then releasing the vial adapter 13. The gripper (G) then positions itself to bear the tip of the vertical linear potentiometer 1136*b* thereof against a shoulder of the vial adapter 13. Rotation is started by rotation station (RS) on the vial assembly, whereby the potentiometer 1136*b* senses a rise of a feature on the vial adapter 13 and halts rotation, so that the vial adapter 13 is now oriented for engagement to a syringe adapter 11. The vial assembly is placed in a holding station, and the gripper (G) returns to the home position.
3. Bring a syringe adapter 11 to the syringe adapter station (SAS). The pair of jaws 1132, 1134 of gripper (G) then engage an upper, outer diameter of a syringe adapter 11 and place the syringe adapter 11 into the syringe adapter station (SAS) by a downward move (e.g., approximated), thus displacing the pair of jaws 1164, 1166 of the syringe adapter station (SAS) so that the pair of jaws 1164, 1166 also engage the outer diameter of the syringe adapter 11. The gripper (G) then releases the syringe adapter 11 and returns the home position.
4. Assemble a syringe "I" to the syringe adapter 11. The pair of jaws 1132, 1134 of gripper (G) then engages a body and a flange of a syringe "I" that has been pre-loaded in the load tray (CH). The gripper (G) then lifts the syringe "I", rotates the syringe "I" about the vertical axis, and presents the syringe "I" to the transfer station (TS), where a plunger of the syringe "I" is retracted to prefill the syringe "I" with air. The gripper (G) then brings the syringe "I" to the syringe adapter station (SAS), where the syringe "I" is moved downward (e.g., approximated) with simultaneous rotation of the syringe adapter 11 to effect the assembly of the luer features therebetween to form a syringe assembly. Rotation then reverses to orient the syringe assembly for connection with the vial adapter 13 of vial assembly. The syringe assembly is then placed in a holding station, and the gripper (G) is returned to the home position.
5. Assembly. The pair of jaws 1132, 1134 of gripper (G) then grasps the vial assembly from the holding station and returns the vial assembly to the rotation station (RS), the pair of jaws 1156, 1158 of the rotation station (RS) then close, and the pair of jaws 1132, 1134 of gripper (G) release. The pair of jaws 1132, 1134 of gripper (G) then takes the syringe assembly and position the syringe assembly over the vial assembly. The wipe station (WS) is then engaged to swing the swing arm 1206 thereof out, to engage the exposed glands or seals of the vial assembly and the syringe assembly. In particular, alcohol is pumped onto the tape (not shown) of wipe station (WS), the tape is precessed, the two exposed glands or seals of respective vial assembly and syringe assembly are then brought into proximity to each other and wiped/sanitized by the tape. The swing arm 1206 then retracts. The vial assembly and the syringe assembly are then pushed together, vertically, to produce a full assembly (e.g., syringe "I", syringe adapter 11, vial adapter 13, and vial "V", all in mechanical and fluid communication with one another).
6. Fluidic transfer. The pair of jaws 1132, 1134 of the gripper (G) then grasps the full assembly, and the gripper (G) then brings the full assembly to the transfer station (TS) for staging therein. The gripper (G) then releases the full assembly, and retracts. A camera of preparation system (not shown), mounted on frame 1100 so as to view the pre-transfer, full assembly, photographically documents the fluidic transfer step. The prefill air (contained in the syringe "I") is pushed into the expansion chamber of the vial adapter 13 by way of advancement of the plunger of syringe "I". The transfer station (TS) is than inverted and the drug (contained in the vial "V") is drawn into the syringe "I" by extension or retraction of the plunger of the syringe "I". The transfer station (TS) then reverts, and the camera documents the transferred condition.
7. Disassembly. The pair of jaws 1132, 1134 of the gripper (G) then engages the full assembly, again by the body and by the flange of the syringe "I" thereof, and then places the full assembly in the rotation station (RS), where the pair of jaws 1156, 1158 of the rotation station (RS) engage the outer diameter of the vial "V" of the full assembly. With the pair of jaws 1132, 1134 of the gripper (G) engaged with the syringe assembly, the pair of jaws 1164, 1166 of the syringe adapter station (SAS) engages a luer neck of the syringe "I", and the syringe assembly is then pulled apart from the vial assembly. The gripper (G) then delivers the syringe assembly to a syringe station of the load tray (CH). The pair of jaws 1132, 1134 of the gripper (G) then disengages from the syringe assembly, the gripper (G) then returns to the rotation station (RS) and the pair of jaws 1132, 1134 of the gripper (G) then engages the vial assembly. The pair of jaws 1156, 1158 of the rotation station (RS) then open, and the gripper (G) then returns the vial assembly to a vial station of the load tray (CH).

The present disclosure contemplates a routine for use on or with an infusion bag (not shown). The infusion bag routine is similar to the push routine, described above, with the exception that step 7 described above is replaced with the following step:

8. Infusion. The pair of jaws 1132, 1134 of the gripper (G) engages the full assembly, again by the body and flange of the syringe "I" thereof, and places the full assembly in the rotation station (RS), where the pair of jaws 1156, 1158 of the rotation station (RS) engage the outer diameter of the vial "V" of the full assembly. With the pair of jaws 1132, 1134 of the gripper (G) engaged with the syringe assembly, the pair of jaws 1164, 1166 of the syringe adapter station (SAS) engages a luer neck of the syringe "I", and the syringe assembly is then pulled apart from the vial assembly, to separate the assemblies from one another. The gripper (G) then separates the syringe assembly and the vial assembly from one another, and brings the syringe assembly to the infusion bag station (IBS) to engage with the I.V. bag adapter 17, by moving syringe assembly vertically downwards (e.g., approximating) onto I.V. bag adapter 17. The pair of jaws 1132, 1134 of the gripper (G) then disengage, travel upwards past the plunger of the syringe "I" to then push against the top of the plunger to transfer the contents of the syringe "I" into the I.V. bag (B). The pair of jaws 1132, 1134 of the gripper (G) then re-engages the syringe assembly and the assemblies are removed as in step 7.

The present disclosure contemplates a routine for reconstitution. The reconstitution routine includes steps 1 through 3, as described above. However, instead of making a prefill, as described in step 4 above, the reconstitution step includes the following step:

9. Assemble syringe components. A syringe "I" is grasped by the pair of jaws 1132, 1134 of the gripper (G) from the load tray (CH) and engaged to a syringe adapter 11, similar to step 4 above.

10. Pull diluent. The gripper (G) brings the syringe assembly to the diluent bag station (DBS) to engage a diluent bag adapter (similar or identical to I.V. bag adapter 17) by moving syringe assembly in a downwards motion (e.g., approximation) towards the diluent bag adapter 17. The pair of jaws 1132, 1134 of the gripper (G) displace the syringe adapter stabilizing arm in the process. The pair of jaws 1132, 1134 of the gripper (G) then releases the syringe "I", the pair of jaws 1132, 1134 of the gripper (G) then engages the plunger of the syringe "I" with barrel grips in the first gripping position (G1) of gripper (G). Diluent is drawn upwards in the syringe "I" by withdrawing the plunger thereof, the pair of jaws 1132, 1134 of the gripper (G) then release the plunger and re-engage the barrel and flange of the syringe "I" of the syringe assembly. The inwards motion of the pair of jaws 1132, 1134 of the gripper (G) displaces the syringe adapter stabilizing arm so that the syringe assembly is withdrawn.

11. Push diluent. The gripper (G) then positions the syringe assembly over the vial assembly, while the vial assembly is in the reconstitution station (W/RS). A wipe is made, by wipe station (WS), to the two exposed glands or seals of respective vial assembly and syringe assembly, similar to that described in 5 above. At this point, the reconstitution routine proceeds to steps 6 and 7, as described above, with the exception that the prefill air of the syringe "I" is not exchanged, since it is not present.

In accordance with the present disclosure, a preparation system 1000 for in-hood compounding is provided. Preparation system 1000 provides an automated approach to the compounding of drugs, in particular dangerous drugs such as some of those used in oncological chemotherapy. Preparation system 1000 is capable of handling drugs in vials, I.V. bags, and the like, within the confines of an engineering control, such as a HEPA washed biological safety cabinet, to provide improved isolation between the operator and the drug. Preparation system 1000 further provides fast, accurate, reliable and repeatable compounding in the interests of increased demand and tight economies.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. An automatic or semi-automatic preparation system for forming a medicament solution from a vial containing one of a liquid and a non-liquid material, the preparation system comprising:
    a frame configured to provide three axes of motion, the frame including:
        a plurality of vertical studs, each stud extending along a respective first axis;
        a plurality of first stringers extending between and interconnecting selected vertical studs, each first stringer extending along a respective second axis, wherein each second axis is orthogonal to the first axis; and
        a plurality of second stringers extending between and interconnecting selected vertical studs and selected first stringers, each second stringer extending along a respective third axis, wherein each third axis is orthogonal to the first axis and orthogonal to the second axis;
    a gantry assembly translatably supported on at least one of the plurality of first stringers;
    a gantry translation assembly operatively connected to the gantry assembly, wherein actuation of the gantry translation assembly causes gantry assembly to translate along the at least one of the plurality of first stringers, in a direction parallel to the second axis; and
    a turntable assembly including:
        a platform translatably supported on gantry assembly;
        a turntable gear supported on the platform, wherein an axis of rotation of the turntable gear extends in a direction parallel to the first axis;
        a rail column depending from and non-rotatably connected to the turntable gear, the rail column extending in a direction parallel to the first axis;

a carriage translatably supported on the rail column;

a carriage motor in operative communication with the carriage, wherein actuation of the carriage motor results in translation of the carriage along the rail column; and a component holder supported on the carriage, the component holder including a gripper having:
 a first pair of fixed, spaced apart jaws, the first pair of jaws including a first jaw and a second jaw; and
 a second pair of fixed, spaced apart jaws, the second pair of jaws including a first jaw and a second jaw;
 wherein the first pair of jaws is translatable relative to the second pair of jaws; and
 wherein the first jaw of the first pair of jaws is interposed between the second pair of jaws, and the second jaw of the second pair of jaws is interposed between the first pair of jaws.

2. The preparation system according to claim 1, wherein the gantry translation assembly includes:
 a threaded gantry rod rotatably supported on the frame, the threaded gantry rod being in threaded engagement with a nut structure of the gantry assembly; and
 a gantry translation motor connected to the threaded gantry rod for rotating the threaded gantry rod in a first direction and a second direction;
 wherein:
  rotation of the gantry translation motor in the first direction causes the gantry assembly to translate in a first direction; and
  rotation of the gantry translation motor in the second direction causes the gantry assembly to translate in a second direction.

3. The preparation system according to claim 2, wherein the gantry assembly includes a nut structure configured to rotatably receive the threaded gantry rod.

4. The preparation system according to claim 3, wherein the gantry translation motor is supported on the frame.

5. The preparation system according to claim 1, wherein the turntable assembly includes:
 a threaded turntable rod rotatably supported on the gantry assembly, the threaded turntable rod being in threaded engagement with a nut structure of the turntable assembly; and
 a turntable translation motor connected to the threaded turntable rod for rotating the threaded turntable rod in a first direction and a second direction;
 wherein:
  rotation of the turntable translation motor in the first direction causes the turntable assembly to translate in a first direction; and
  rotation of the turntable translation motor in the second direction causes the turntable assembly to translate in a second direction.

6. The preparation system according to claim 5, wherein the turntable assembly includes a nut structure configured to rotatably receive the threaded turntable rod.

7. The preparation system according to claim 6, wherein the turntable translation motor is supported on the gantry assembly.

8. The preparation system according to claim 1, wherein the gantry assembly includes a turntable rotation motor supported thereon, wherein the turntable rotation motor is operatively connected to the turntable gear to cause the turntable gear to rotate in a first direction and a second direction.

9. The preparation system according to claim 1, wherein operation of the gripper includes translation of the first pair of jaws relative to the second pair of jaws to grip a component at:
 a first gripping position located between the first jaw of the first pair of jaws and the first jaw of the second pair of jaws;
 a second gripping position located between the second jaw of the first pair of jaws and the first jaw of the second pair of jaws; and
 a third gripping position located between the second jaw of the first pair of jaws and the second jaw of the second pair of jaws.

\* \* \* \* \*